(12) United States Patent
Hoeng et al.

(10) Patent No.: US 10,916,350 B2
(45) Date of Patent: *Feb. 9, 2021

(54) SYSTEMS AND METHODS FOR QUANTIFYING THE IMPACT OF BIOLOGICAL PERTURBATIONS

(71) Applicant: PHILIP MORRIS PRODUCTS S.A., Neuchâtel (CH)

(72) Inventors: Julia Hoeng, Corcelles (CH); Florian Martin, Peseux (CH); Manuel Claude Peitsch, Peseux (CH); Alain Sewer, Orbe (CH)

(73) Assignee: Philip Morris Products S.A., Neuchâtel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/385,351

(22) Filed: Dec. 20, 2016

(65) Prior Publication Data

US 2017/0235914 A1    Aug. 17, 2017

Related U.S. Application Data

(63) Continuation of application No. 14/124,799, filed as application No. PCT/EP2012/061033 on Jun. 11, 2012, now Pat. No. 9,558,318.

(Continued)

(30) Foreign Application Priority Data

Dec. 22, 2011 (EP) .................................. 11195417

(51) Int. Cl.
*G16H 50/50*     (2018.01)
*G16B 5/00*      (2019.01)
(Continued)

(52) U.S. Cl.
CPC .............. *G16H 50/50* (2018.01); *G06N 5/02* (2013.01); *G06N 7/005* (2013.01); *G06N 7/06* (2013.01); *G16B 5/00* (2019.02); *G16B 40/00* (2019.02)

(58) Field of Classification Search
CPC ..... G06F 19/12; G06F 19/3456; G16B 40/00; G16B 45/00; G16H 50/50
See application file for complete search history.

(56) References Cited

U.S. PATENT DOCUMENTS 5,640,494 A * 6/1997 Jabri ...................... G06N 3/084
706/25
6,132,969 A * 10/2000 Stoughton ............... G06F 19/12
435/4

(Continued)

FOREIGN PATENT DOCUMENTS

WO    WO 2012/168481    12/2012
WO    WO 2012/168483    12/2012

(Continued)

OTHER PUBLICATIONS

Anonymous: Dot product—Wikipedia, the free encyclopedia, retrieved from the Internet: URL:http//en.wikipedia.org/w/index.php?title=Dot_product&oldid=551038540 [retrieved on Jul. 21, 2014].

(Continued)

*Primary Examiner* — Amresh Singh
(74) *Attorney, Agent, or Firm* — Sterne, Kessler, Goldstein & Fox P.L.L.C.

(57) ABSTRACT

Systems and methods are described for quantifying the response of a biological system to one or more perturbations. First and second datasets corresponding to a response of a biological system to first and second treatments are received. A plurality of computational network models that represent the biological system are provided, each model including nodes representing a plurality of biological entities and (Continued)

edges representing relationships between the nodes in the model. A first set of scores is generated, representing the perturbation of the biological system based on the first dataset and the plurality of models, and a second set of scores representing the perturbation of the biological system based on the second dataset and the plurality of computational models. One or more biological impact factors are generated based on each of the first set and second set of scores that represent the biological impact of the perturbation on the biological system.

20 Claims, 13 Drawing Sheets

Related U.S. Application Data

(60) Provisional application No. 61/495,824, filed on Jun. 10, 2011, provisional application No. 61/525,700, filed on Aug. 19, 2011.

(51) Int. Cl.
*G16B 40/00* (2019.01)
*G06N 5/02* (2006.01)
*G06N 7/06* (2006.01)
*G06N 7/00* (2006.01)

(56) References Cited

U.S. PATENT DOCUMENTS

| | | | |
|---|---|---|---|
| 7,599,933 B2 | 10/2009 | Domany et al. | |
| 8,068,994 B2* | 11/2011 | Drăghici | G06F 19/12 435/5 |
| 8,518,649 B2* | 8/2013 | Southern | G01N 33/6893 435/7.1 |
| 8,577,619 B2* | 11/2013 | Sander | G06F 19/12 702/19 |
| 8,594,941 B2 | 11/2013 | Chandra et al. | |
| 9,558,318 B2 | 1/2017 | Hoeng et al. | |
| 2003/0143520 A1* | 7/2003 | Hood | G06F 19/18 435/4 |
| 2005/0165594 A1* | 7/2005 | Chandra | G16B 5/00 703/11 |
| 2005/0240563 A1 | 10/2005 | Domany et al. | |
| 2007/0016390 A1* | 1/2007 | Bernardo | G06F 19/12 703/11 |
| 2007/0225956 A1* | 9/2007 | Pratt | G06F 19/12 703/11 |
| 2008/0195322 A1 | 8/2008 | Altschuler et al. | |
| 2008/0195332 A1 | 8/2008 | Wong et al. | |
| 2009/0099784 A1* | 4/2009 | Ladd | G16B 5/00 702/19 |
| 2009/0117589 A1 | 5/2009 | Southern | |
| 2009/0182513 A1 | 7/2009 | Draghici | |
| 2010/0299289 A1 | 11/2010 | Simha et al. | |
| 2011/0119259 A1 | 5/2011 | Collins et al. | |
| 2011/0191087 A1* | 8/2011 | Lehrach | G06F 19/12 703/11 |
| 2014/0114987 A1 | 4/2014 | Hoeng et al. | |
| 2014/0172398 A1 | 6/2014 | Hoeng et al. | |
| 2016/0063176 A1 | 3/2016 | Martin et al. | |

FOREIGN PATENT DOCUMENTS

WO   WO 2013/034300    3/2013
WO   WO 2014/173912   10/2014

OTHER PUBLICATIONS

Anonymous: Resampling (statistics)—Wikipedia, the free encyclopedia, retrieved from the Internet: URL:http//en.wikipedia.org/w/index.php?title=Resampling_(statistics)&oldid-551416561#Permutation_tests [retrieved on Jul. 18, 2014].

Gimenez, Local influence analysis based on the perturbation manifold in functional measurement error models http://www.matematica.uns.edu.ar/Xcongresomonteiro/actas.HTM (May 29, 2009).

Herrgard, Reconciling gene expression data with known genome-scale regulatory network structures, Genome Res. 13(11):2423-2434 (2003).

Hoeng et al., A network-based approach to quantifying the impact of biologically active substances, Drug Discovery today 17(9-10):413-418 (2012).

Hoeng et al., Case study: the role of mechanistic network models in systems toxicology, Drug Discovery Today 19(2):183-192 (2014).

International Search Report and Written Opinion for PCT/EP2012/061033 dated Aug. 28, 2012.

International Search Report and Written Opinion for PCT/EP2012/061035 dated Aug. 28, 2012.

International Search Report and Written Opinion for PCT/EP2014/058159 dated Jul. 29, 2014.

Martin et al., Assessment of network perturbation amplitudes by applying high throughput data to causal biological networks, BMC Systems Biol. 6:54-71 (2012).

Schlage et al., A computable cellular stress network model for non-diseased pulmonary and cardiovascular tissue, BMC Systems Biol. 5:168-182 (2011).

Selventa, Reverse causal reasoning method—White Paper, 26 pp. http://www.selventa.com/attachments/white_papers/reverse-causal-reasoning.pdf (Feb. 4, 2011).

Strimmer, A unified approach to false discover rate estimation, BMC Bioinformatics, Biomed Central 9(1):303 (2008).

Westra et al., Construction of a computable cell proliferation network focused on non-diseased lung cells, BMC Systems Biol. 5(1):105-105 (2011).

Friedman et al., "Data analysis with bayesian networks: A bootstrap approach," in Uncertainty in Artificial Intelligence 196-205 (1999).

Friedman et al., "Using bayesian networks to analyze expression data," Journal of Computational Biology, 7:601-620 (2000).

Ishwaran et al., "Detecting differentially expressed genes in microarrays using bayesian model selection," Journal of the American Statistical Association, 98:438-455 (2003).

Lofroth et al. "Ah receptor ligands in tobacco smoke," Toxicology Letters, 42:131-136 (1988).

Schrenk, "Impact of dioxin-type induction of drug-metabolizing enzymes on the metabolism of endo- and xenobiotics," Biochemical Pharmacology, 55:1155-1162 (1998).

Spiegelhalter et al., "Bayesian measures of model complexity and fit," Journal of the Royal Statistical Society Series B, 64:583-639 (2002).

Toyoshiba et al., "Gene interaction network suggests dioxin induces a significant linkage between aryl hydrocarbon receptor and retinoic acid receptor beta," Environmental Health Perspectives, 112:1217-1224 (2004).

U.S. Appl. No. 14/124,826 Non-Final Office Action dated Apr. 11, 2016.

* cited by examiner

|  | NET-1 908 | NET-2 910 | NET-3 912 |
|---|---|---|---|
| SHORT 902 | $S_{SHORT}^1$ | $S_{SHORT}^2$ | $S_{SHORT}^3$ |
| MEDIUM 904 | $S_{MEDIUM}^1$ | $S_{MEDIUM}^2$ | $S_{MEDIUM}^3$ |
| LONG 906 | $S_{LONG}^1$ | $S_{LONG}^2$ | $S_{LONG}^3$ |
|  | $c_1$ | $c_2$ | $c_3$  } 914 |

SYSTEMS AND METHODS FOR QUANTIFYING THE IMPACT OF BIOLOGICAL PERTURBATIONS

CROSS REFERENCE TO RELATED APPLICATIONS

This application is a continuation of U.S. patent application Ser. No. 14/124,799, filed Dec. 13, 2013, (allowed), which is a U.S. Nationalization of PCT Application Number PCT/EP2012/061033 filed Jun. 11, 2012, which claims the benefit of U.S. Provisional Application No. 61/495,824 filed Jun. 10, 2011, U.S. Provisional Application No. 61/525,700 filed Aug. 19, 2011, and European Application 11195417.8 filed Dec. 22, 2011, the entireties of which are incorporated herein by reference.

BACKGROUND

The human body is constantly perturbed by exposure to potentially harmful agents that can pose severe health risks in the long-term. Exposure to these agents can compromise the normal functioning of biological mechanisms internal to the human body. To understand and quantify the effect that these perturbations have on the human body, researchers study the mechanism by which biological systems respond to exposure to agents. Some groups have extensively utilized in vivo animal testing methods. However, animal testing methods are not always sufficient because there is doubt as to their reliability and relevance. Numerous differences exist in the physiology of different animals. Therefore, different species may respond differently to exposure to an agent. Accordingly, there is doubt as to whether responses obtained from animal testing may be extrapolated to human biology. Other methods include assessing risk through clinical studies of human volunteers. But these risk assessments are performed a posteriori and, because diseases may take decades to manifest, these assessments may not be sufficient to elucidate mechanisms that link harmful substances to disease. Yet other methods include in vitro experiments. Although, in vitro cell and tissue-based methods have received general acceptance as full or partial replacement methods for their animal-based counterparts, these methods have limited value. Because in vitro methods are focused on specific aspects of cells and tissues mechanisms; they do not always take into account the complex interactions that occur in the overall biological system.

In the last decade, high-throughput measurements of nucleic acid, protein and metabolite levels in conjunction with traditional dose-dependent efficacy and toxicity assays, have emerged as a means for elucidating mechanisms of action of many biological processes. Researchers have attempted to combine information from these disparate measurements with knowledge about biological pathways from the scientific literature to assemble meaningful biological modes. To this end, researchers have begun using mathematical and computational techniques that can mine large quantities of data, such as clustering and statistical methods, to identify possible biological mechanisms of action.

Previous work has also explored the importance of uncovering a characteristic signature of gene expression changes that results from one or more perturbations to a biological process, and the subsequent scoring of the presence of that signature in additional data sets as a measure of the specific activity amplitude of that process. Most work in this regard has involved identifying and scoring signatures that are correlated with a disease phenotype. These phenotype-derived signatures provide significant classification power, but lack a mechanistic or causal relationship between a single specific perturbation and the signature. Consequently, these signatures may represent multiple distinct unknown perturbations that, by often unknown mechanism(s), lead to, or result from, the same disease phenotype.

One challenge lies in understanding how the activities of various individual biological entities in a biological system enable the activation or suppression of different biological mechanisms. Because an individual entity, such as a gene, may be involved in multiple biological processes (e.g., inflammation and cell proliferation), measurement of the activity of the gene is not sufficient to identify the underlying biological process that triggers the activity.

None of the current techniques have been applied to perform predictive risk-assessment and to address the relationship between short-term exposure to a perturbation and long-term disease outcomes. Typically, this question is addressed by traditional longitudinal epidemiological studies, but such studies may present ethical challengers and cannot satisfy the currently pressing need for risk assessment. In fact, for new agents, traditional longitudinal epidemiological techniques simply cannot be used. Accordingly, there is a need for improved systems and methods for studying the impact of perturbations on the human body.

SUMMARY ASPECTS AND EMBODIMENTS

Described herein are systems, methods and products for quantifying the response of a biological system to one or more perturbations based on measured activity data from a subset of the entities in the biological system.

In one aspect, there is provided a computerized method for determining the impact of a perturbation on a biological system, comprising: receiving, at a processor, a first dataset corresponding to a response of a biological system to a first treatment, wherein the biological system comprises a plurality of biological entities wherein each biological entity in the biological system interacts with at least one other biological entities in the biological system; receiving, at a processor, a second dataset corresponding to a response of the biological system to a second treatment different from the first treatment; providing, at a processor, a plurality of computational network models that represent the biological system, each model including nodes representing a plurality of biological entities and edges representing relationships between the nodes in the model; generating, at a processor, a first set of scores representing the perturbation of the biological system based on the first dataset and the plurality of models, and a second set of scores representing the perturbation of the biological system based on the second dataset and the plurality of computational models; and generating, at a processor, one or more biological impact factor(s) based on each of the first set and second set of scores that represent the biological impact of the perturbation on the biological system.

In one embodiment, more than two datasets are received and a corresponding number of sets of scores are generated. In certain embodiments, more than three, more than four, more than five, more than six, more than seven, more than eight, more than nine or more than ten datasets are received. In certain embodiments, at least as many datasets as there are perturbations or treatments are received.

In one embodiment, a biological impact factor is generated for each of the treatments.

In one embodiment, at least one of the datasets comprises treatment data and corresponding control data.

In one embodiment, at least one of the plurality of networks is a causal network.

In one embodiment, the scores within each set of scores are calculated independently by a geometric perturbation index scoring technique, a probabilistic perturbation index scoring technique or an expected perturbation index scoring technique In one embodiment, each of the scores within the first set and second set of scores includes a score vector, and the step of generating a biological impact factor further comprises filtering, at a processor, the first score and the second score to decompose each of the first and second scores into a plurality of projections onto a set of basis vectors.

In one embodiment, filtering further comprises removing, from at least one of the decomposed first and second scores, at least one of the plurality of projections.

In one embodiment, the set of basis vectors comprise the eigenvectors of a matrix descriptive of at least one of the models.

In one embodiment, generating the first set and second set of scores comprises: assigning, at a processor, a weight for each of the scores within the first set and second set of scores based on the corresponding computational network model and at least one of the first dataset and the second dataset; aggregating the weighted scores of the first set of scores; aggregating the weighted scores of the second set of scores; wherein the one or more biological impact factor is a function of the aggregated scores of the first set of scores and of the second set of scores.

In one embodiment, the one or more biological impact factors is a linear combination, a linear transformation, or a quadratic form of the aggregated scores of the first and second set of scores.

In one embodiment, assigning a weight for each of the scores within the first set and second set of scores comprises selecting a weight for each of the plurality of computational models to maximize the difference between the scores within the first set of scores and the scores within the second set of scores.

In one embodiment, generating a biological impact factor comprises determining an inner product between a first vector representative of the aggregated score of the first set of scores and a second vector representative of the aggregated score of the second set of scores.

In one embodiment, generating a biological impact factor comprises determining a distance between a first surface defined by a first vector representative of the aggregated score of a first set of scores and a second surface defined by a second vector representative of the aggregated second set of scores.

In one embodiment, the computational network models are selected from two or more of a Cell Proliferation Network, an Inflammatory Process Network, a Cellular Stress Network and a DNA Damage, Autophagy, Cell Death and Senescence Network.

In a further aspect, there is described a computer system for determining a biological impact factor, the computer system comprising a processor configured to: receive first data corresponding to a response of a set of biological entities to a first treatment, wherein a biological system comprises a plurality of biological entities including the set of biological entities and wherein each biological entity in the biological system interacts with at least one other of the biological entities in the biological system; receive second data corresponding to a response of the set of biological entities to a second treatment different from the first treatment; provide a plurality of computational causal network models that represent the biological system, each computational model including nodes representing the plurality of biological entities and edges representing relationships between entities in the plurality of biological entities; generate a first score representing the perturbation of the biological system based on the first data and the plurality of computational models, and a second score representing the perturbation of the biological system based on the second data and the plurality of computational models; and generate a biological factor based on the first and second scores.

In one embodiment, each of the first and second scores includes a score vector, and wherein the processor is further configured to: filter the first and second scores to decompose each of the first and second scores into a plurality of projections onto a set of basis vectors; and remove, from at least one of the first and second scores, at least one of the plurality of projections.

In one embodiment, the set of basis vectors comprise the eigenvectors of a matrix descriptive of at least one of the computational models or wherein generating a biological impact factor comprises determining an inner product between a first vector representative of the first score and a second vector representative of the second score.

In one embodiment, generating a biological impact factor comprises determining a distance between a first surface representative of the first score and a second surface representative of the second score.

In one embodiment, the biological system includes at least one of a cell proliferation mechanism, a cellular stress mechanism, a cell inflammation mechanism, and a DNA repair mechanism.

In one embodiment, the first treatment includes at least one of exposure of aerosol generated by heating tobacco, exposure to aerosol generated by combusting tobacco, exposure to tobacco smoke, exposure to cigarette smoke, exposure to a heterogeneous substance including a molecule or an entity that is not present in or derived from the biological system, and exposure to at least one of toxins, therapeutic compounds, stimulants, relaxants, natural products, manufactured products, food substances and exposure to one or more of cadmium, mercury, chromium, nicotine, tobacco-specific nitrosamines and their metabolites (4-(methylnitrosamino)-1-(3-pyridyl)-1-butanone (NNK), N'-nitrosonornicotine (NNN), N-nitrosoanatabine (NAT), N-nitrosoanabasine (NAB), and 4-(methylnitrosamino)-1-(3-pyridyl)-1-butanol (NNAL)).

In a further aspect, there is described a computer program product comprising a program code adapted to perform the method disclosed herein.

In a further aspect, there is described a computer or a computer recordable medium comprising the computer program product.

In a further aspect, there is provided a method for determining the biological impact of a perturbation on a biological system, comprising: generating one or more biological impact factors that represent the biological impact of a perturbation on a biological system, wherein at least one of the biological impact factors is determined according to the computerized method described herein; comparing the one or more biological impact factors with one or more biological impact factors that have been obtained in the absence of the perturbation or in the presence of a different perturbation; and wherein the comparison is indicative of the biological impact of the perturbation on the biological system.

In a further aspect, there is provided a computerized method for determining the biological impact of a perturbation on a biological system, comprising: generating one or more biological impact factors that represent the biological impact of a perturbation on a biological system, wherein at least one of the biological impact factors is determined according to the computerized method of any of claims 1 to 15, 21 or 22; comparing the one or more biological impact factors with one or more biological impact factors that have been obtained in the absence of the perturbation or in the presence of a different perturbation; and wherein the comparison is indicative of the biological impact of the perturbation on the biological system.

In a further aspect, there is provided a method for determining the biological impact of a perturbation on a biological system, comprising: generating one or more biological impact factors that represent the biological impact of a perturbation on a biological system, wherein at least one of the biological impact factors is determined by using the method described herein; comparing the one or more biological impact factors with one or more biological impact factors that have been obtained in the absence of the perturbation or in the presence of a different perturbation; and wherein the comparison is indicative of the biological impact of the perturbation on the biological system.

In one embodiment, the biological impact factor(s) is used to estimate or determine the magnitude of, desirable or adverse biological effects caused by pathogens, harmful substances, manufactured products, manufactured products for safety assessment or risk-of-use comparisons, therapeutic compounds or changes in the environment or environmentally active substances.

In one embodiment, two or more different perturbations are used to compare the impact of the different perturbations on the biological system.

In one embodiment, the perturbation(s) represent at least two different treatment conditions.

In one embodiment, at least one of the treatments includes at least one of aerosol generated by heating tobacco, exposure to aerosol generated by combusting tobacco, exposure to tobacco smoke, exposure to cigarette smoke, exposure to a heterogeneous substance including a molecule or an entity that is not present in or derived from the biological system, and exposure to at least one of toxins, therapeutic compounds, stimulants, relaxants, natural products, manufactured products, and food substances.

In one embodiment, the perturbation is caused by one or more agents.

In one embodiment, the agent is selected from the group consisting of aerosol generated by heating tobacco, aerosol generated by combusting tobacco, tobacco smoke, cigarette smoke, and any of the gaseous constituents or particulate constituents thereof, cadmium, mercury, chromium, nicotine, tobacco-specific nitrosamines and their metabolites (such as 4-(methylnitrosamino)-1-(3-pyridyl)-1-butanone (NNK), N'-nitrosonornicotine (NNN), N-nitrosoanatabine (NAT), N-nitrosoanabasine (NAB and 4-(methylnitrosamino)-1-(3-pyridyl)-1-butanol (NNAL)) or a combination of one or more thereof.

In one embodiment, at least one of the biological impact factors has been previously determined or previously calculated.

In another aspect, there is provided a computerized method for determining the impact of a perturbation on a biological system, comprising: receiving, at a processor, first data corresponding to a response of a set of biological entities to a first treatment, wherein a biological system comprises a plurality of biological entities including the set of biological entities and wherein each biological entity in the biological system interacts with at least one other of the biological entities in the biological system; receiving, at a processor, second data corresponding to a response of the set of biological entities to a second treatment different from the first treatment; providing, at a processor, a plurality of computational causal network models that represent a biological system, each computational model including nodes representing the plurality of biological entities and edges representing relationships between entities in the plurality of biological entities; generating, at a processor, a first score representing the perturbation of the biological system based on the first data and the plurality of computational models, and a second score representing the perturbation of the biological system based on the second data and the plurality of computational models; and generating, at a processor, a biological impact factor based on the first and second scores that represents the biological impact of the perturbation on the biological system.

In one embodiment, each of the first and second scores includes a score vector, and the step of generating a biological impact factor further comprises filtering, at a processor, the first score and the second score to decompose each of the first and second scores into a plurality of projections onto a set of basis vectors.

In one embodiment, the filtering further comprises removing, from at least one of the decomposed first and second scores, at least one of the plurality of projections.

In one embodiment, the set of basis vectors comprise the eigenvectors of a matrix descriptive of at least one of the computational models.

In one embodiment, generating the first and second scores comprises: assigning, at a processor, a weight for each of the plurality of computational models based on the corresponding computational model and at least one of the first data and the second data; generating, at a processor, a plurality of first scores corresponding to the plurality of computational models and based on the first data; generating, at a processor, a plurality of second scores corresponding to the plurality of computational models and based on the second data; combining the plurality of first scores according to the assigned weights; combining the plurality of second scores according to the assigned weights; wherein the biological impact factor is a function of the combined plurality of first scores and the combined plurality of second scores.

In one embodiment, determining a weight for each of the plurality of computational models comprises selecting a weight for each of the plurality of computational models to maximize a difference between the plurality of first scores and the plurality of second scores.

In one embodiment, generating a biological impact factor comprises determining an inner product between a first vector representative of the first score and a second vector representative of the second score.

In one embodiment, generating a biological impact factor comprises determining a distance between a first surface representative of the first score and a second surface representative of the second score.

In one embodiment, the computational causal network models are selected from two or more of a Cell Proliferation Network, an Inflammatory Process Network, a Cellular Stress Network and a DNA Damage, Autophagy, Cell Death and Senescence Network.

In a further aspect there is provided a computer system for determining a biological impact factor comprising means adapted for carrying out the computerized method.

In one embodiment, the computer system comprises a processor configured to: receive first data corresponding to a response of a set of biological entities to a first treatment, wherein a biological system comprises a plurality of biological entities including the set of biological entities and wherein each biological entity in the biological system interacts with at least one other of the biological entities in the biological system; receive second data corresponding to a response of the set of biological entities to a second treatment different from the first treatment; provide a plurality of computational causal network models that represent the biological system, each computational model including nodes representing the plurality of biological entities and edges representing relationships between entities in the plurality of biological entities; generate a first score representing the perturbation of the biological system based on the first data and the plurality of computational models, and a second score representing the perturbation of the biological system based on the second data and the plurality of computational models; and generate a biological impact factor based on the first and second scores.

In one embodiment, each of the first and second scores includes a score vector, and wherein the processor is further configured to: filter the first and second scores to decompose each of the first and second scores into a plurality of projections onto a set of basis vectors; and remove, from at least one of the first and second scores, at least one of the plurality of projections.

In one embodiment, the set of basis vectors comprise the eigenvectors of a matrix descriptive of at least one of the computational models.

In one embodiment, a biological impact factor is generated which comprises determining an inner product between a first vector representative of the first score and a second vector representative of the second score.

In one embodiment, generating a biological impact factor comprises determining a distance between a first surface representative of the first score and a second surface representative of the second score.

In one embodiment, the biological system includes at least one of a cell proliferation mechanism, a cellular stress mechanism, a cell inflammation mechanism, and a DNA repair mechanism.

In one embodiment, the first treatment includes at least one of aerosol generated by heating tobacco, exposure to aerosol generated by combusting tobacco, exposure to tobacco smoke, exposure to cigarette smoke, exposure to a heterogeneous substance including a molecule or an entity that is not present in or derived from the biological system, and exposure to at least one of toxins, therapeutic compounds, stimulants, relaxants, natural products, manufactured products, and food substances.

In a further aspect, there is provided a computer program product comprising a program code adapted to perform the computerized method of the present invention.

In a further aspect, there is provided a computer or a computer recordable medium comprising the computer program product of the present invention.

In one aspect, the systems and methods described herein are directed to computerized methods (for example, computer implemented methods) and one or more computer processors for quantifying the impact of a perturbation on a biological system (for example, in response to a treatment condition such as agent exposure, or in response to multiple treatment conditions). A processor receives first data corresponding to a response of a set of biological entities to a first treatment. The set of biological entities is part of a plurality of biological entities that are included in a biological system. Each biological entity in the biological system interacts with at least one other of the biological entities in the biological system. A processor also receives second data corresponding to a response of the set of biological entities to a second treatment different from the first treatment. A processor also provides a plurality of computational causal network models that represent the biological system. Each computational model including nodes representing the plurality of biological entities and edges representing relationships between entities in the plurality of biological entities.

A processor then generates a first score representing the perturbation of the biological system based on the first data and the plurality of computational models, and a second score representing the perturbation of the biological system based on the second data and the plurality of computational models. A processor then generates a "biological impact factor" or "BIF" based on the first and second scores. In various implementations, the computerized method combines a plurality of model scores corresponding to the plurality of treatments (or agents) and generates a BIF that represents the relative biological effects caused by the treatments (or agents). In some implementations, generating a biological impact factor comprises determining an inner product between a first vector representative of the first score and a second vector representative of the second score. In some implementations, generating a biological impact factor comprises determining a distance between a first surface representative of the first score and a second surface representative of the second score.

In some implementations, each of the first and second scores includes a score vector, and the step of generating a biological impact factor further comprises filtering, at a processor, the first score and the second score to decompose each of the first and second scores into a plurality of projections onto a set of basis vectors. Filtering may further include removing, from at least one of the decomposed first and second scores, at least one of the plurality of projections. The set of basis vectors comprise the eigenvectors of a matrix descriptive of at least one of the computational models, such as the Laplacian matrix.

In some implementations, generating the first and second scores includes assigning a weight for each of the plurality of computational models based on the corresponding computational model and at least one of the first data and the second data. A weight may be assigned, for example, to maximize a difference between the plurality of first scores and the plurality of second scores. A processor may further generate a plurality of first scores corresponding to the plurality of computational models and based on the first data and a plurality of second scores corresponding to the plurality of computational models and based on the second data. The processor may then combine the plurality of first scores according to the assigned weights and combine the plurality of second scores according to the assigned weights. In some such implementations, the biological impact factor is a function of the combined plurality of first scores and the combined plurality of second scores.

In certain implementations, the biological system includes, but is not limited to, at least one of a cell proliferation mechanism, a cellular stress mechanism, a cell inflammation mechanism, a DNA repair mechanism, a DNA damage mechanism, an autophagy mechanism, a cell death mechanism and a senescence mechanism. The treatment may include, but is not limited to, exposure to a heterogeneous substance, including a molecule or an entity that is not present in or derived from the biological system. The treatment may include, but is not limited to, exposure to toxins, therapeutic compounds, stimulants, relaxants, natural products, manufactured products, and food substances. The treatment may include, but is not limited to, exposure to at least one of aerosol generated by heating tobacco, aerosol generated by combusting tobacco, tobacco smoke, and cigarette smoke. The treatment may include, but is not limited to, exposure to cadmium, mercury, chromium, nicotine, tobacco-specific nitrosamines and their metabolites (4-methylnitrosamino)-1-(3-pyridyl)-1-batanone (NNK), N'-nitrosonornicotine (NNN), N-nitrosoanatabine (NAT), N-nitrosoanabasine (NAB), and 4-(methylnitrosamino)-1-(3-pyridyl)-1-butanol (NNAL)). In certain implementations, the agent includes a product used for nicotine replacement therapy.

The computerized methods described herein may be implemented in a computerized system having one or more computing devices, each including one or more processors. Generally, the computerized systems described herein may comprise one or more engines, which include a processing device or devices, such as a computer, microprocessor, logic device or other device or processor that is configured with hardware, firmware, and software to carry out one or more of the computerized methods described herein. In certain implementations, the computerized system includes a systems response profile engine, a network modeling engine, and a network scoring engine. The engines may be interconnected from time to time, and further connected from time to time to one or more databases, including a perturbations database, a measurables database, an experimental data database and a literature database. The computerized system described herein may include a distributed computerized system having one or more processors and engines that communicate through a network interface. Such an implementation may be appropriate for distributed computing over multiple communication systems.

BRIEF DESCRIPTION OF THE DRAWINGS

Further features of the disclosure, its nature and various advantages will be apparent upon consideration of the following detailed description, taken in conjunction with the accompanying drawings, in which like reference characters refer to like parts throughout, and in which:

FIG. 9 illustrates an example of network weighting during network response score aggregation;

DETAILED DESCRIPTION

Figure 1:
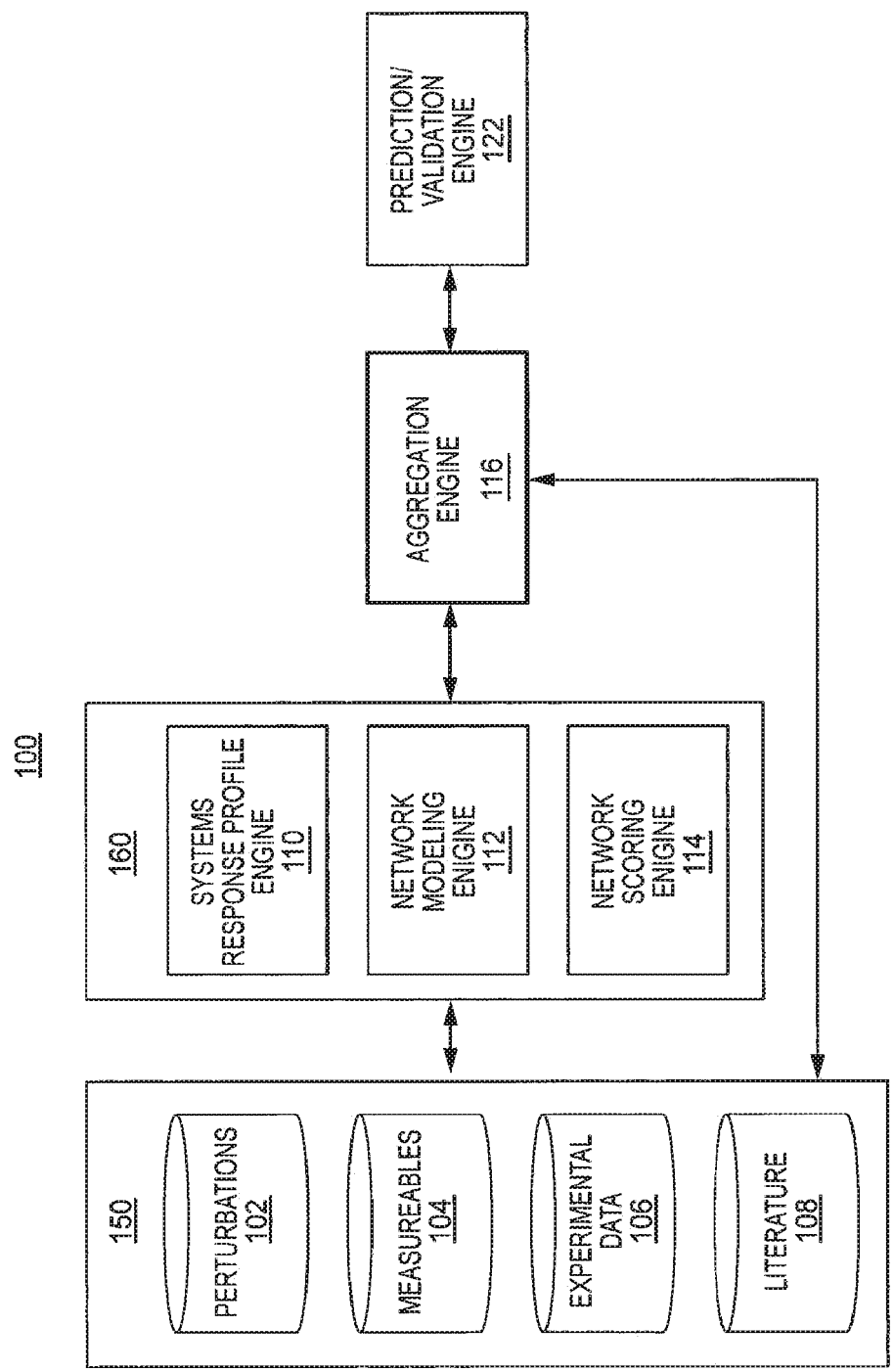
FIG. 1 is a block diagram of an illustrative computerized system for quantifying the impact of a biological perturbation.

Described herein are computational systems and methods that assess and express quantitatively the impact of a perturbation on a biological system. Certain implementations of the present disclosure include methods for computing a numerical value (referred to herein as a biological impact factor, or BIF) that expresses the overall impact of a perturbation on a biological system. Computer systems for executing these computational methods are also provided as are methods for determining the impact of a perturbation on a biological system by comparing biological impact factors.

Prior knowledge of a biological system and its functional features are encoded in one or more databases which are used to construct network models representative of aspects of the biological system. Methods for creating such databases and network models are known in the art and can be used in conjunction with methods of the present disclosure. In simulating an aspect of a biological system, the network model is populated by data on the status or activity of a plurality of biological entities in the biological system under various conditions, including normal conditions, controlled or control conditions, or treatment conditions such as when it is perturbed by an agent. Data regarding the status or activity of various biological entities when the biological system is perturbed by an agent can be compared to and analyzed with data in the model(s) which had been obtained under normal or controlled conditions. The network model(s) are dynamic in that they represent changes in the status or activity of various biological entities in response to a perturbation and can yield quantitative and objective assessments of the impact of an agent on the biological system.

The computational methods described herein use sets of data obtained from controlled experiments in which a biological system is perturbed. In certain embodiments, a plurality of datasets are obtained from measurements of changes in various aspects or functional features of the biological system after exposure to an agent. A plurality of datasets can also be obtained by making measurements of the biological entities when exposed to an agent under different exposure conditions, such as but not limited to, length of time of exposure, frequency of exposure, concentration of the agent, and part(s) of the biological system being exposed, and optionally under different measurement conditions, such as time elapsed after last exposure. Because an agent can affect more than one functional feature of a biological system, a plurality of datasets are analyzed in the context of a plurality of network models of the biological system. Each network model is used as a substrate for simulation and analysis of a dataset resulting in numerical values, generally referred to herein as network response scores. The number of network models—such as at least two network models—may correspond to the number of network response scores. Each network model can correspond to a functional feature of the biological system or represent a biological mechanism or biochemical pathway that enables certain functions of the biological system. The activities associated with such functional features, mechanisms or pathways of the biological system are collectively a manifest of the status of the biological system. Such biological mechanisms or biochemical pathways may each play a role in the maintenance of a healthy biological system or in the pathology of certain diseases or adverse health effects. The computerized methods described herein aggregate a plurality of network response scores, taking into account the relative contribution of each network to the overall status of the biological system, to produce a numerical value, i.e., a BIF given a plurality of datasets. In certain implementations, the computerized methods described herein also include the generation of network response scores.

The BIFs generated by the computerized methods disclosed herein can be used to estimate or determine the magnitude of desirable or adverse biological effects caused by any external factors, including but not limited to pathogens (for diagnosis or prognosis of diseases), harmful substances (for toxicological assessment), manufactured products (for safety assessment or risk-of-use comparisons), therapeutic compounds including nutrition supplements (for determination of efficacy or health benefits), and changes in the environment or environmentally active substances (for public health assessment, e.g., pollutants or ultraviolet light from the sun). The BIF can be used for prediction of the biological risks of acute, intermittent or sustained exposure, and the relationship to immediate or long term adverse effects on the biological system and onset of disease(s). The perturbation is a cause that is external to the biological system in question. BIF values obtained for different agents or different types of perturbations can be used to compare relatively the impact of the different agents or perturbations on a biological system. A BIF can be used as a predictor for medium and long term disease outcome, optionally the value can be calibrated using a combination of experimental and epidemiological data. BIF values are computed by using any of various mathematical and computational algorithms known in the art according to the methods disclosed herein, employing one or more datasets obtained from one or more sample or subject.

A BIF value can be computed which represents the differential response of a biological system to at least two different treatment conditions. A BIF value can be computed which represents the differential response of a biological system to more than two different treatment conditions— such as a plurality of different treatment conditions. At least one of the treatments may be a control for one or more of the other treatments. When a plurality of different treatment conditions are used then two or more controls may be used. Each treatment may have one or more controls. The number of treatments may correspond to the number of datasets. The number of treatments may correspond to the number of BIFs. At least one relative BIF may exist for two or more treatments. In some embodiments, a first treatment condition can be a perturbation regarded as an experimental treatment (such as but not limited to exposure to a potentially carcinogenic agent) and a second treatment condition regarded as a control (such as a null treatment). In some embodiments, a first treatment condition can be a perturbation regarded as a first experimental treatment (such as but not limited to exposure to a first potentially carcinogenic agent) and a second treatment can be a perturbation regarded as a second experimental treatment (such as but not limited to exposure to a second potentially carcinogenic agent). In some embodiments, a first treatment condition can be a perturbation of a first biological system regarded as a first experimental treatment (such as but not limited to exposure to a potentially carcinogenic agent) and a second treatment can be a perturbation of a second biological system regarded as a second experimental treatment (such as but not limited to exposure to the same potentially carcinogenic agent). Thus, in this embodiment, the biological impact of the treatment on the biological system—such as a human—is determined. In further embodiments, the impact on a plurality of biological systems can be determined. In further embodiments, the impact of an agent on a plurality of biological systems can be determined. In further embodiments, the impact of a plurality of agents on a plurality of biological systems can be determined. In some embodiments, the BIF computed to represent the impact of a first agent in a biological system can be used for comparison with the BIF representing the impact of a second agent in the same biological system. The numerical scores can thus be used to assess and compare the differential effects of two or more agents on a biological system or certain features thereof. Accordingly, a plurality of datasets is obtained from measurements of changes in the biological system after it has been exposed respectively to a plurality of different agents.

FIG. 1 is a block diagram of a computerized system 100 for quantifying the biological impact of one or more perturbations. In particular, system 100 includes a systems response profile engine 110, a network modeling engine 112, a network scoring engine 114 and an aggregation engine 116. The engines 110, 112, 114 and 116 are interconnected from time to time, and further connected from time to time to one or more databases, including a perturbations database 102, a measurable database 104, an experimental data database 106 and a literature database 108. As used herein, an engine includes a processing device or devices, such as a computer, microprocessor, logic device, or other device or devices as described with reference to FIG. 12 that is configured with hardware, firmware and/or software to carry out one or more of the computational techniques described herein.

During operation, for a given perturbation, the system 100 generates a biological impact factor (BIF), which is a quantitative measure of the impact, including long-term impact of that perturbation on a biological system including the human body. More particularly, the system 100 generates or provides computerized models for one or more biological systems and mechanisms (collectively, "biological networks") relevant to the type of perturbation, a desired biological mechanism of interest or a particular long-term outcome of interest. For example, the system 100 may generate or provide a computational model for the mechanism of cell proliferation when the cells have been exposed to cigarette smoke. In such an example, the system 100 may also generate or provide one or more computational models representative of the different stages of a disease, including but not limited to cancer, pulmonary disease and cardiovascular disease. In certain aspects, the system 100 generates these computerized models based on at least one of the perturbations applied (e.g., exposure to an agent), the measureable quantities of interest, the outcome being studied (e.g., cell proliferation, cellular stress, inflammation, DNA repair), experimental data and knowledge obtained from scientific literature. The system 100 measures and quantifies the effect of the treatment to generate a BIF. The prediction/validation engine 122 may receive one or more BIF values and may use these BIF values to make outcome predictions (e.g., the decrease in cancer incidence or likelihood when a toxic substance is removed from the human environment). The prediction/validation engine 122 may also or alternatively compare the BIF values to known biological outcomes to calibrate the BIF values or validate the predictions of the BIF values. An example of a calibration and validation is illustrated by the results shown in FIG. 13 below. The various components and engines of system 100 include at least one of hardware and software components and will be further described with reference to FIGS. 11 and 12.

Figure 2:
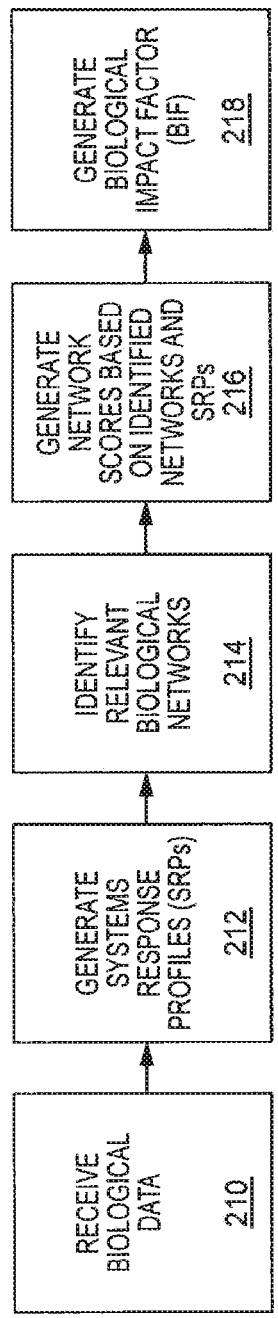
FIG. 2 is a flow diagram of an illustrative process for generating a biological impact factor (BIF).

FIG. 2 is a flow diagram of a process 200 for quantifying the impact of a perturbation on a biological system by calculating a biological impact factor (BIF), according to one implementation. The steps of the process 200 will be described as being carried out by various components of the system 100 of FIG. 1, but any of these steps may be performed by any suitable hardware or software components, local or remote, and may be arranged in any appropriate order or performed in parallel. At step 210, the systems response profile (SRP) engine 110 receives biological data from a variety of different sources, and the data itself may be of a variety of different types. In some implementations of step 210, the SRP engine 110 receives first data corresponding to a response of a set of biological entities to a first treatment and receives second data corresponding to a response of the set of biological entities to a second treatment different from the first treatment. For example, the data received at step 210 may include data from experiments in which a biological system is perturbed by exposure to an agent or environmental condition, and may also include control data.

A biological system in the context of the present disclosure is an organism or a part of an organism, including functional parts, the organism being referred to herein as a subject. The subject is generally a mammal, including a human. The subject can be an individual human being in a human population. The term "mammal" as used herein includes but is not limited to a human, non-human primate, mouse, rat, dog, cat, cow, sheep, horse, and pig. Mammals other than humans can be advantageously used as subjects that can be used to provide a model of a human disease. The non-human subject can be unmodified, or a genetically modified animal (e.g., a transgenic animal, or an animal carrying one or more genetic mutation(s), or silenced gene(s)). A subject can be male or female. Depending on the objective of the operation, a subject can be one that has been exposed to an agent of interest. A subject can be one that has been exposed to an agent over an extended period of time, optionally including time prior to the study. A subject can be one that had been exposed to an agent for a period of time but is no longer in contact with the agent. A subject can be one that has been diagnosed or identified as having a disease. A subject can be one that has already undergone, or is undergoing treatment of a disease or adverse health condition. A subject can also be one that exhibits one or more symptoms or risk factors for a specific health condition or disease. A subject can be one that is predisposed to a disease, and may be either symptomatic or asymptomatic. In certain implementations, the disease or health condition in question is associated with exposure to an agent or use of an agent over an extended period of time. According to some implementations, the system 100 (FIG. 1) contains or generates computerized models of one or more biological systems and mechanisms of its functions (collectively, "biological networks" or "network models") that are relevant to a type of perturbation or an outcome of interest.

Depending on the context of the operation, the biological system can be defined at different levels as it relates to the function of an individual organism in a population, an organism generally, an organ, a tissue, a cell type, an organelle, a cellular component, or a specific individual's cell(s). Each biological system comprises one or more biological mechanisms or pathways, the operation of which manifest as functional features of the system. Animal systems that reproduce defined features of a human health condition and that are suitable for exposure to an agent of interest are preferred biological systems. Cellular and organotypical systems that reflect the cell types and tissue involved in a disease etiology or pathology are also preferred biological systems. Priority could be given to primary cells or organ cultures that recapitulate as much as possible the human biology in vivo. It is also important to match the human cell culture in vitro with the most equivalent culture derived from the animal models in vivo. This enables creation of a translational continuum from animal model to human biology in vivo using the matched systems in vitro as reference systems. Accordingly, the biological system contemplated for use with the systems and methods described herein can be defined by, without limitation, functional features (biological functions, physiological functions, or cellular functions), organelle, cell type, tissue type, organ, development stage, or a combination of the foregoing. Examples of biological systems include, but are not limited to, the pulmonary, integument, skeletal, muscular, nervous (central and peripheral), endocrine, cardiovascular, immune, circulatory, respiratory, urinary, renal, gastrointestinal, colorectal, hepatic and reproductive systems. Other examples of biological systems include, but are not limited to, the various cellular functions in epithelial cells, nerve cells, blood cells, connective tissue cells, smooth muscle cells, skeletal muscle cells, fat cells, ovum cells, sperm cells, stem cells, lung cells, brain cells, cardiac cells, laryngeal cells, pharyngeal cells, esophageal cells, stomach cells, kidney cells, liver cells, breast cells, prostate cells, pancreatic cells, islet cells, testes cells, bladder cells, cervical cells, uterus cells, colon cells, and rectum cells. Some of the cells may be cells of cell lines, cultured in vitro or maintained in vitro indefinitely under appropriate culture conditions. Examples of cellular functions which can also be considered as a functional feature of a biological system include, but are not limited to, cell proliferation (e.g., cell division), degeneration, regeneration, senescence, control of cellular activity by the nucleus, cell-to-cell signaling, cell differentiation, cell de-differentiation, secretion, migration, phagocytosis, repair, apoptosis, and developmental programming. Examples of cellular components that can be considered as biological systems include, but are not limited to, the cytoplasm, cytoskeleton, membrane, ribosomes, mitochondria, nucleus, endoplasmic reticulum (ER), Golgi apparatus, lyosomes, DNA, RNA, proteins, peptides, and antibodies.

A perturbation in a biological system can be caused by one or more agents over a period of time through exposure or contact with one or more parts of the biological system. An agent can be a single substance or a mixture of substances, including a mixture in which not all constituents are identified or characterized. The chemical and physical properties of an agent or its constituents may not be fully characterized. An agent can be defined by its structure, its constituents, or a source that under certain defined conditions produces the agent. An example of an agent is a heterogeneous substance, that is a molecule or an entity that is not present in or derived from the biological system, and any intermediates or metabolites produced therefrom after contacting the biological system. An agent can be a carbohydrate, protein, lipid, nucleic acid, alkaloid, vitamin, metal, heavy metal, mineral, oxygen, ion, enzyme, hormone, neurotransmitter, inorganic chemical compound, organic chemical compound, environmental agent, microorganism, particle, environmental condition, environmental force, or physical force. Non-limiting examples of agents include but are not limited to nutrients, metabolic wastes, poisons, narcotics, toxins, therapeutic compounds, stimulants, relaxants, natural products, manufactured products, food substances, pathogens (prion, virus, bacteria, fungi, protozoa), particles or entities whose dimensions are in or below the micrometer range, by-products of the foregoing and mixtures of the foregoing. Non-limiting examples of a physical agent include radiation, electromagnetic waves (including sunlight), increase or decrease in temperature, shear force, fluid pressure, electrical discharge(s) or a sequence thereof, or trauma.

Some agents may not perturb a biological system unless it is present at a threshold concentration or it is in contact with the biological system for a period of time, or a combination of both. Exposure or contact of an agent resulting in a perturbation may be quantified in terms of dosage. Thus, a perturbation can result from a long-term exposure to an agent. The period of exposure can be expressed by units of time, by frequency of exposure, or by the percentage of time within the actual or estimated life span of the subject. A perturbation can also be caused by withholding an agent (as described above) from or limiting supply of an agent to one or more parts of a biological system. For example, a perturbation can be caused by a decreased supply of or a lack of nutrients, water, carbohydrates, proteins, lipids, alkaloids, vitamins, minerals, oxygen, ions, an enzyme, a hormone, a neurotransmitter, an antibody, a cytokine, light, or by restricting movement of certain parts of an organism, or by constraining or requiring exercise.

An agent may cause different perturbations depending on which part(s) of the biological system is exposed and the exposure conditions. Non-limiting examples of an agent may include aerosol generated by heating tobacco, aerosol generated by combusting tobacco, tobacco smoke, cigarette smoke, and any of the gaseous constituents or particulate constituents thereof. Further non-limiting examples of an agent include cadmium, mercury, chromium, nicotine, tobacco-specific nitrosamines and their metabolites (such as 4-(methylnitrosamino)-1-(3-pyridyl)-1-butanone (NNK), N'-nitrosonornicotine (NNN), N-nitrosoanatabine (NAT), N-nitrosoanabasine (NAB), and 4-(methylnitrosamino)-1-(3-pyridyl)-1-butanol (NNAL)), and any product used for nicotine replacement therapy. An exposure regimen for an agent or complex stimulus should reflect the range and circumstances of exposure in everyday settings. A set of standard exposure regimens can be designed to be applied systematically to equally well-defined experimental systems. Each assay could be designed to collect time and dose-dependent data to capture both early and late events and ensure a representative dose range is covered. However, it will be understood by one of ordinary skill in the art that the systems and methods described herein may be adapted and modified as is appropriate for the application being addressed and that the systems and methods designed herein may be employed in other suitable applications, and that such other additions and modifications will not depart from the scope thereof.

In various implementations, high-throughput system-wide measurements for gene expression, protein expression or turnover, microRNA expression or turnover, post-translational modifications, protein modifications, translocations, antibody production metabolite profiles, or a combination of two or more of the foregoing are generated under various conditions including the respective controls. Functional outcome measurements are desirable in the methods described herein as they can generally serve as anchors for the assessment and represent clear steps in a disease etiology.

A "sample" as used herein refers to any biological sample that is isolated from a subject or an experimental system (e.g., cell, tissue, organ, or whole animal). A sample can include, without limitation, a single cell or multiple cells, cellular fraction, tissue biopsy, resected tissue, tissue extract, tissue, tissue culture extract, tissue culture medium, exhaled gases, whole blood, platelets, serum, plasma, erythrocytes, leucocytes, lymphocytes, neutrophils, macrophages, B cells or a subset thereof, T cells or a subset thereof, a subset of hematopoietic cells, endothelial cells, synovial fluid, lymphatic fluid, ascites fluid, interstitial fluid, bone marrow, cerebrospinal fluid, pleural effusions, tumor infiltrates, saliva, mucous, sputum, semen, sweat, urine, or any other bodily fluids. Samples can be obtained from a subject by means including but not limited to venipuncture, excretion, biopsy, needle aspirate, lavage, scraping, surgical resection, or other means known in the art.

During operation, for a given biological mechanism, an outcome, a perturbation, or a combination of the foregoing, the system 100 can generate a network response score, which is a quantitative measure of changes in the status of biological entities in a network in response to a treatment condition. The number of scores in a set of scores may correspond to the number of networks.

The system 100 (FIG. 1) comprises one or more computerized network model(s) that are relevant to the health condition, disease, or biological outcome, of interest. One or more of these network models are based on prior biological knowledge and can be uploaded from an external source and curated within the system 100. The models can also be generated de novo within the system 100 based on measurements. Measurable elements are casually integrated into biological network models through the use of prior knowledge. Described below are the types of data that represent changes in a biological system of interest that can be used to generate or refine a network model, or that represent a response to a perturbation.

Returning to FIG. 2, at step 210, the systems response profile (SRP) engine 110 receives biological data. The SRP engine 110 may receive this data from a variety of different sources, and the data itself may be of a variety of different types. The biological data used by the SRP engine 110 may be drawn from the literature, databases (including data from preclinical, clinical and post-clinical trials of pharmaceutical products or medical devices), genome databases (genomic sequences and expression data, e.g., Gene Expression Omnibus by National Center for Biotechnology Information or ArrayExpress by European Bioinformatics Institute (Parkinson et al. 2010, Nucl. Acids Res., doi: 10.1093/nar/gkq1040. Pubmed ID 21071405)), commercially available databases (e.g., Gene Logic, Gaithersburg, Md., USA) or experimental work. The data may include raw data from one or more different sources, such as in vitro, ex vivo or in vivo experiments using one or more species that are specifically designed for studying the effect of particular treatment conditions or exposure to particular agents. In vitro experimental systems may include tissue cultures or organotypical cultures (three-dimensional cultures) that represent key aspects of human disease. In such implementations, the agent dosage and exposure regimens for these experiments may substantially reflect the range and circumstances of exposures that may be anticipated for humans during normal use or activity conditions, or during special use or activity conditions. Experimental parameters and test conditions may be selected as desired to reflect the nature of the agent and the exposure conditions, molecules and pathways of the biological system in question, cell types and tissues involved, the outcome of interest, and aspects of disease etiology. Particular animal-model-derived molecules, cells or tissues may be matched with particular human molecule, cell or tissue cultures to improve translatability of animal-based findings.

The data received by SRP engine 110 many of which are generated by high-throughput experimental techniques, include but are not limited to that relating to nucleic acid (e.g., absolute or relative quantities of specific DNA or RNA species, changes in DNA sequence, RNA sequence, changes in tertiary structure, or methylation pattern as determined by sequencing, hybridization—particularly to nucleic acids on microarray, quantitative polymerase chain reaction, or other techniques known in the art), protein/peptide (e.g., absolute or relative quantities of protein, specific fragments of a protein, peptides, changes in secondary or tertiary structure, or posttranslational modifications as determined by methods known in the art) and functional activities (e.g., enzymatic activities, proteolytic activities, transcriptional regulatory activities, transport activities, binding affinities to certain binding partners) under certain conditions, among others. Modifications including posttranslational modifications of protein or peptide can include, but are not limited to, methylation, acetylation, farnesylation, biotinylation, stearoylation, formylation, myristoylation, palmitoylation, geranylgeranylation, pegylation, phosphorylation, sulphation, glycosylation, sugar modification, lipidation, lipid modification, ubiquitination, sumolation, disulphide bonding, cysteinylation, oxidation, glutathionylation, carboxylation, glucuronidation, and deamidation. In addition, a protein can be modified posttranslationally by a series of reactions such as Amadori reactions, Schiff base reactions, and Maillard reactions resulting in glycated protein products.

The data may also include measured functional outcomes, such as but not limited to those at a cellular level including cell proliferation, developmental fate, and cell death, at a physiological level, lung capacity, blood pressure, exercise proficiency. The data may also include a measure of disease activity or severity, such as but not limited to tumor metastasis, tumor remission, loss of a function, and life expectancy at a certain stage of disease. Disease activity can be measured by a clinical assessment the result of which is a value, or a set of values that can be obtained from evaluation of a sample (or population of samples) from a subject or subjects under defined conditions. A clinical assessment can also be based on the responses provided by a subject to an interview or a questionnaire.

This data may have been generated expressly for use in determining a systems response profile, or may have been produced in previous experiments or published in the literature. Generally, the data includes information relating to a molecule, biological structure, physiological condition, genetic trait, or phenotype. In some implementations, the data includes a description of the condition, location, amount, activity, or substructure of a molecule, biological structure, physiological condition, genetic trait, or phenotype. As will be described later, in a clinical setting, the data may include raw or processed data obtained from assays performed on samples obtained from human subjects or observations on the human subjects, exposed to an agent.

Figure 3:
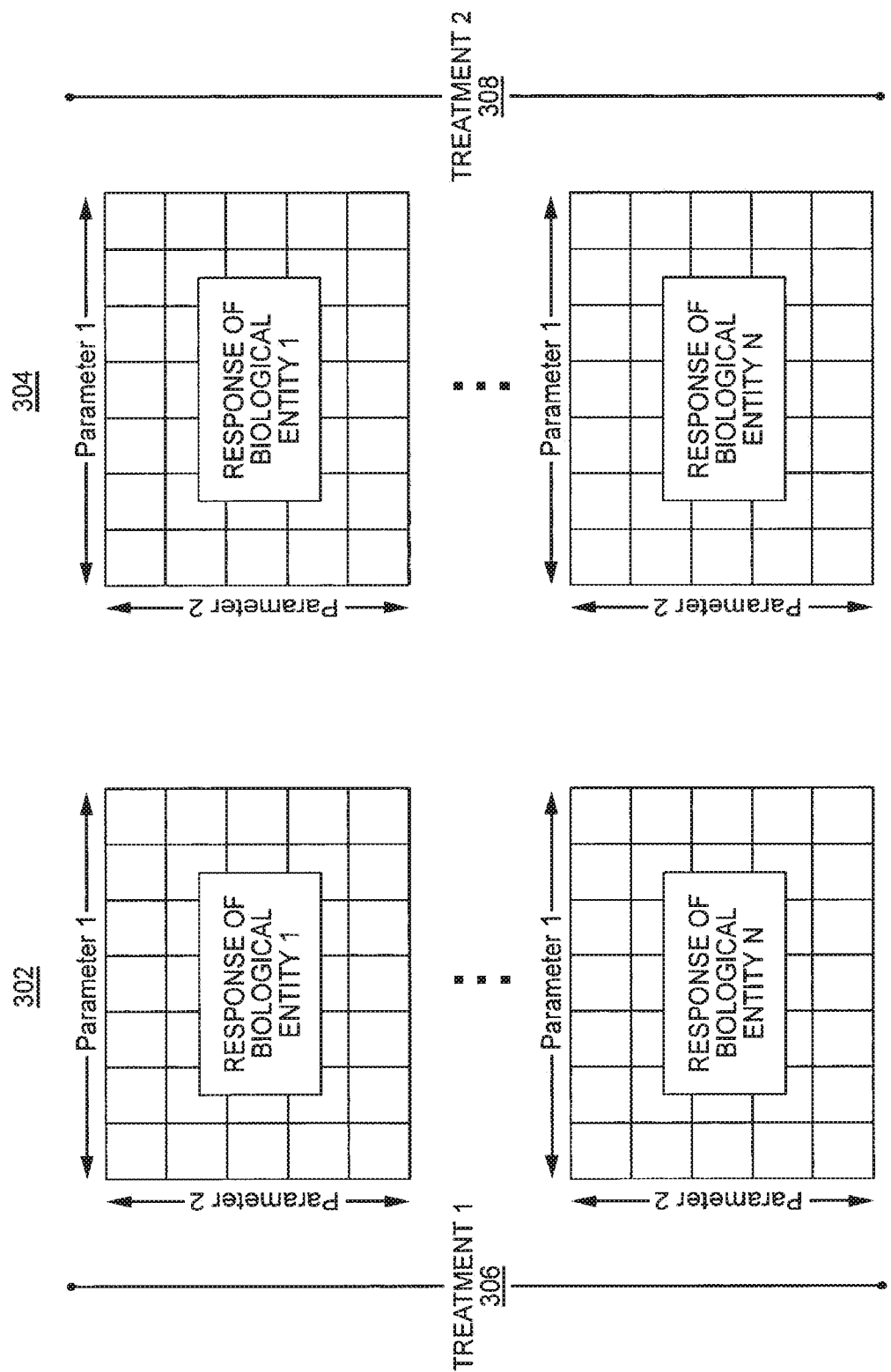
FIG. 3 is a graphical representation of data underlying a systems response profile comprising data for two agents, two parameters, and N biological entities.

At step 212, the systems response profile (SRP) engine 110 generates systems response profiles (SRPs) based on the biological data received at step 212. SRPs are representations that express the degree to which one or more measured entities within a biological system (e.g., a molecule, a nucleic acid, a peptide, a protein, a cell, etc.) are individually changed in response to a perturbation applied to the biological system (e.g., an exposure to an agent). This step may include one or more of background correction, normalization, fold-change calculation, significance determination and identification of a differential response (e.g., differentially expressed genes). In one example, to generate an SRP, the SRP engine 110 collects a set of measurements for a given set of parameters (e.g., treatment or perturbation conditions) applied to a given experimental system (a "system-treatment" pair). FIG. 3 illustrates two SRPs: SRP 302 that includes biological activity data for N different biological entities undergoing a first treatment 306 with varying parameters (e.g., dose and time exposure to a first treatment agent), and an analogous SRP 304 that includes biological activity data for the N different biological entities undergoing a second treatment 308. The data included in an SRP may be raw experimental data, processed experimental data (e.g., filtered to remove outliers, marked with confidence estimates, averaged over a number of trials), data generated by a computational biological model, or data taken from the scientific literature. An SRP may represent data in any number of ways, such as an absolute value, an absolute change, a fold-change, a logarithmic change, a function, and a table. The SRP engine 110 passes the SRPs to the network modeling engine 112.

At step 214, the network modeling engine 112 provides a plurality of computational models of a biological system that includes the biological entities for which data was received at step 210. Each computational model includes nodes representing the biological entities and edges representing the relationships between biological entities in the biological system. The network modeling engine 112 may derive these computational models from one or more databases that contain(s) a plurality of network models, one of which is selected as being relevant to the agent or a feature of interest. The selection can be made on the basis of prior knowledge of the mechanisms underlying the biological functions of the system. In certain implementations, the network modeling engine 112 may extract causal relationships between entities within the system using the systems response profiles, networks in the database, and networks previously described in the literature, thereby generating, refining or extending a network model.

In some implementations of step 214, the network modeling engine 112 uses the systems response profiles from the SRP engine 110 with a network model that is based on the mechanism(s) or pathway(s) underlying a feature of interest in a biological system. While the SRPs derived in the previous step represent the experimental data from which the magnitude of network perturbation will be determined, it is the biological network models that are the substrate for computation and analysis. This analysis requires the initial development of a detailed network model of the mechanisms and pathways relevant to a feature of the biological system. Such a framework provides a layer of mechanistic understanding beyond examination of gene lists that have been used in more classical gene expression analysis. A network model of a biological system is a mathematical construct that is representative of a dynamic biological system and that is built by assembling quantitative information about various basic properties of the biological system.

Construction of such a network may be an iterative process. Delineation of boundaries of the network is guided by reviewing the scientific literature on the mechanisms and pathways relevant to a feature of interest (e.g., cell proliferation in the lung). Causal relationships describing these pathways are extracted from prior knowledge to nucleate a network. The literature-based network can be verified using high-throughput data sets that contain the relevant phenotypic endpoints. SRP engine 110 can be used to analyze the data sets, the results of which can be used to confirm, refine, or generate network models. In some implementations, the network modeling engine 112 is used to identify networks already generated based on SRPs. The network modeling engine 112 may include components for receiving updates and changes to models. The network modeling engine 112 may iterate the process of network generation by incorporating new data and generating additional or refined network models. The network modeling engine 112 may also facilitate the merging of one or more datasets or the merging of one or more networks. The set of networks drawn from a database may be manually supplemented by additional nodes, edges, or entirely new networks (e.g., by mining the text of literature for description of additional genes directly regulated by a particular biological entity). These networks contain features that may enable process scoring. Network topology is maintained; networks of causal relationships can be traced from any point in the network to a measurable entity. Further, the models are dynamic and the assumptions used to build them can be modified or restated and enable adaptability to different tissue contexts and species. This allows for iterative testing and improvement as new knowledge becomes available. The network modeling engine 112 may remove nodes or edges that have low confidence or which are the subject of conflicting experimental results in the scientific literature. The network modeling engine 112 may also include additional nodes or edges that may be inferred using supervised or unsupervised learning methods (e.g., metric learning, matrix completion, pattern recognition).

Figure 4:
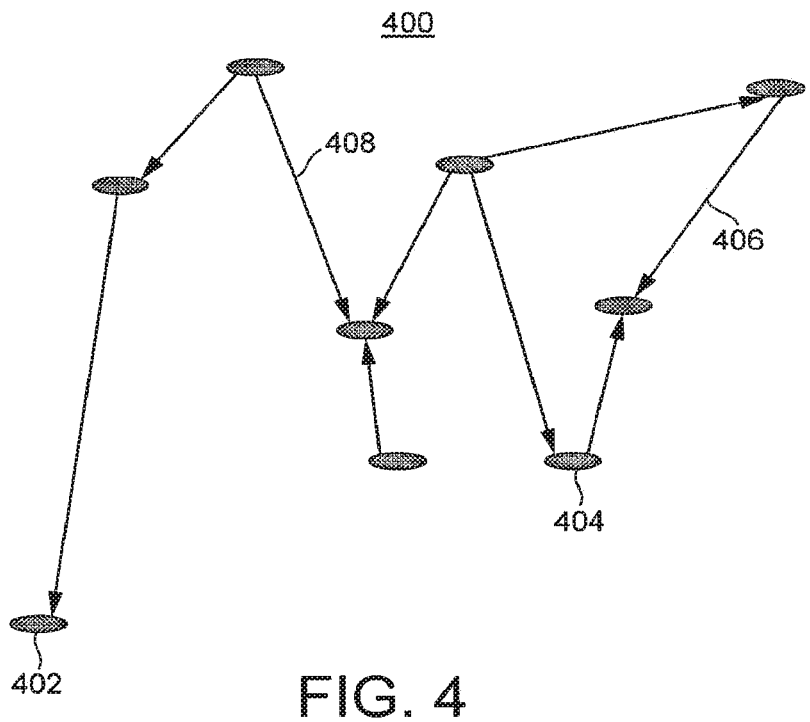
FIG. 4 is an illustration of a computational model of a biological network having several biological entities and their relationships.

In certain aspects, a biological system is modeled as a mathematical graph consisting of vertices (or nodes) and edges that connect the nodes. For example, FIG. 4 illustrates a simple network 400 with 9 nodes (including nodes 402 and 404) and edges (406 and 408). The nodes can represent biological entities within a biological system, such as, but not limited to, compounds, DNA, RNA, proteins, peptides, antibodies, cells, tissues, and organs. The edges can represent relationships between the nodes. The edges in the graph can represent various relations between the nodes. For example, edges may represent a "binds to" relation, an "is expressed in" relation, an "are co-regulated based on expression profiling" relation, an "inhibits" relation, a "co-occur in a manuscript" relation, or "share structural element" relation. Generally, these types of relationships describe a relationship between a pair of nodes. The nodes in the graph can also represent relationships between nodes. Thus, it is possible to represent relationships between relationships, or relationships between a relationship and another type of biological entity represented in the graph. For example a relationship between two nodes that represent chemicals may represent a reaction. This reaction may be a node in a relationship between the reaction and a chemical that inhibits the reaction.

A graph may be undirected, meaning that there is no distinction between the two vertices associated with each edge. Alternatively, the edges of a graph may be directed from one vertex to another. For example, in a biological context, transcriptional regulatory networks and metabolic networks may be modeled as a directed graph. In a graph model of a transcriptional regulatory network, nodes would represent genes with edges denoting the transcriptional relationships between them. As another example, protein-protein interaction networks describe direct physical interactions between the proteins in an organism's proteome and there is often no direction associated with the interactions in such networks. Thus, these networks may be modeled as undirected graphs. Certain networks may have both directed and undirected edges. The entities and relationships (i.e., the nodes and edges) that make up a graph, may be stored as a web of interrelated nodes in a database in system 100.

The knowledge represented within the database may be of various different types, drawn from various different sources. For example, certain data may represent a genomic database, including information on genes, and relations between them. In such an example, a node may represent an oncogene, while another node connected to the oncogene node may represent a gene that inhibits the oncogene. The data may represent proteins, and relations between them, diseases and their interrelations, and various disease states. There are many different types of data that can be combined in a graphical representation. The computational models may represent a web of relations between nodes representing knowledge in, e.g., a DNA dataset, an RNA dataset, a protein dataset, an antibody dataset, a cell dataset, a tissue dataset, an organ dataset, a medical dataset, an epidemiology dataset, a chemistry dataset, a toxicology dataset, a patient dataset, and a population dataset. As used herein, a dataset is a collection of numerical values resulting from evaluation of a sample (or a group of samples) under defined conditions. Datasets can be obtained, for example, by experimentally measuring quantifiable entities of the sample; or alternatively, or from a service provider such as a laboratory, a clinical research organization, or from a public or proprietary database. Datasets may contain data and biological entities represented by nodes, and the nodes in each of the datasets may be related to other nodes in the same dataset, or in other datasets. Moreover, the network modeling engine 112 may generate computational models that represent genetic information, in, e.g., DNA, RNA, protein or antibody dataset, to medical information, in medical dataset, to information on individual patients in patient dataset, and on entire populations, in epidemiology dataset. In addition to the various datasets described above, there may be many other datasets, or types of biological information that may be included when generating a computation model. For example, a database could further include medical record data, structure/activity relationship data, information on infectious pathology, information on clinical trials, exposure pattern data, data relating to the history of use of a product, and any other type of life science-related information. The network modeling engine 112 may generate one or more network models representing, for example, the regulatory interaction between genes, interaction between proteins or complex bio-chemical interactions within a cell or tissue. The networks generated by the network modeling engine 112 may include static and dynamic models. The network modeling engine 112 may employ any applicable mathematical schemes to represent the system, such as hypergraphs and weighted bipartite graphs, in which two types of nodes are used to represent reactions and compounds. The network modeling engine 112 may also use other inference techniques to generate network models, such as an analysis based on over-representation of functionally-related genes within the differentially expressed genes, Bayesian network analysis, a graphical Gaussian model technique or a gene relevance network technique, to identify a relevant biological network based on a set of experimental data (e.g., gene expression, metabolite concentrations, cell response, etc.).

As described above, the network model is based on mechanisms and pathways that underlie the functional features of a biological system. The network modeling engine 112 may generate or contain a model representative of an outcome regarding a feature of the biological system that is relevant to the study of the long-term health risks or health benefits of agents. Accordingly, the network modeling engine 112 may generate or contain a network model for various mechanisms of cellular function, particularly those that relate or contribute to a feature of interest in the biological system, including but not limited to cellular proliferation, cellular stress, cellular regeneration, apoptosis, DNA damage/repair or inflammatory response. In other embodiments, the network modeling engine 112 may contain or generate computational models that are relevant to acute systemic toxicity, carcinogenicity, dermal penetration, cardiovascular disease, pulmonary disease, ecotoxicity, eye irrigation/corrosion, genotoxicity, immunotoxicity, neurotoxicity, pharmacokinetics, drug metabolism, organ toxicity, reproductive and developmental toxicity, skin irritation/corrosion or skin sensitization. Generally, the network modeling engine 112 may contain or generate computational models for status of nucleic acids (DNA, RNA, SNP, siRNA, miRNA, RNAi), proteins, peptides, antibodies, cells, tissues, organs, and any other biological entity, and their respective interactions. In one example, computational network models can be used to represent the status of the immune system and the functioning of various types of white blood cells during an immune response or an inflammatory reaction. In other examples, computational network models could be used to represent the performance of the cardiovascular system and the functioning and metabolism or endothelial cells.

In some implementations of the present disclosure, the network is drawn from a database of causal biological knowledge. This database may be generated by performing experimental studies of different biological mechanisms to extract relationships between mechanisms (e.g., activation or inhibition relationships), some of which may be causal relationships, and may be combined with a commercially-available database such as the Genstruct Technology Platform or the Selventa Knowledgebase, curated by Selventa Inc. of Cambridge, Mass., USA. Using a database of causal biological knowledge, the network modeling engine 112 may identify a network that links the perturbations 102 and the measurables 104. In certain implementations, the network modeling engine 112 extracts causal relationships between biological entities using the systems response profiles from the SRP engine 110 and networks previously generated in the literature. The database may be further processed to remove logical inconsistencies and generate new biological knowledge by applying homologous reasoning between different sets of biological entities, among other processing steps.

In certain implementations, the network model built from information extracted from the database is based on reverse causal reasoning (RCR), an automated reasoning technique that processes networks of causal relationships to formulate mechanism hypotheses, and then evaluates those mechanism hypotheses against datasets of differential measurements. Each mechanism hypothesis links a biological entity to measurable quantities that it can influence. For example, measurable quantities can include an increase or decrease in concentration, number or relative abundance of a biological entity, activation or inhibition of a biological entity, or changes in the structure, function or logical of a biological entity, among others. RCR uses a directed network of experimentally-observed causal interactions between biological entities as a substrate for computation. The directed network may be expressed in Biological Expression Language™ (BEL™), a syntax for recording the inter-relationships between biological entities. The RCR computation specifies certain constraints for network model generation, such as but not limited to path length (the maximum number of edges connecting an upstream node and downstream nodes), and possible causal paths that connect the upstream node to downstream nodes. The output of RCR is a set of mechanism hypotheses that represent upstream controllers of the differences in experimental measurements, ranked by statistics that evaluate relevance and accuracy. The mechanism hypotheses output can be assembled into causal chains and larger networks to interpret the dataset at a higher level of interconnected mechanisms and pathways.

One type of mechanism hypothesis comprises a set of causal relationships that exist between a node representing a potential cause (the upstream node or controller) and nodes representing the measured quantities (the downstream nodes). This type of mechanism hypothesis can be used to make predictions, such as if the abundance of an entity represented by an upstream node increase, the downstream nodes linked by causal increase relationships would be inferred to be increase, and the downstream nodes linked by causal decrease relationships would be inferred to decrease.

A mechanism hypothesis represents the relationships between a set of measured data, for example, gene expression data, and a biological entity that is a known controller of those genes. Additionally, these relationships include the sign (positive or negative) of influence between the upstream entity and the differential expression of the downstream entities (for example, downstream genes). The downstream entities of a mechanism hypothesis can be drawn from a database of literature-curated causal biological knowledge. In certain implementations, the causal relationships of a mechanism hypothesis that link the upstream entity to downstream entities, in the form of a computable causal network model, are the substrate for the calculation of network changes by the network response scoring methods.

In certain embodiments, a complex causal network model of biological entities can be transformed into a single causal network model by collecting the individual mechanism hypothesis representing various features of the biological system in the model and regrouping the connections of all the downstream entities (e.g., downstream genes) to a single upstream entity or process, thereby representing the whole complex causal network model; this in essence is a flattening of the underlying graph structure. Changes in the features and entities of a biological system as represented in a network model can thus be assessed by combining individual mechanism hypotheses.

In certain implementations, the system 100 may contain or generate a computerized model for the mechanism of cell proliferation when the cells have been exposed to cigarette smoke. In such an example, the system 100 may also contain or generate one or more network models representative of the various health conditions relevant to cigarette smoke exposure, including but not limited to cancer, pulmonary diseases and cardiovascular diseases. In certain aspects, these network models are based on at least one of the perturbations applied (e.g., exposure to an agent), the responses under various conditions, the measureable quantities of interest, the outcome being studied (e.g., cell proliferation, cellular stress, inflammation, DNA repair), experimental data, clinical data, epidemiological data, and literature.

As an illustrative example, the network modeling engine 112 may be configured for generating a network model of cellular stress. The network modeling engine 112 may receive networks describing relevant mechanisms involved in the stress response known from literature databases. The network modeling engine 112 may select one or more networks based on the biological mechanisms known to operate in response to stresses in pulmonary and cardiovascular contexts. In certain implementations, the network modeling engine 112 identifies one or more functional units within a biological system and builds a larger network model by combining smaller networks based on their functionality. In particular, for a cellular stress model, the network modeling engine 112 may consider functional units relating to responses to oxidative, genotoxic, hypoxic, osmotic, xenobiotic, and shear stresses. Therefore, the network components for a cellular stress model may include xenobiotic metabolism response, genotoxic stress, endothelial shear stress, hypoxic response, osmotic stress and oxidative stress. The network modeling engine 112 may also receive content from computational analysis of publicly available transcriptomic data from stress relevant experiments performed in a particular group of cells.

When generating a network model of a biological mechanism, the network modeling engine 112 may include one or more rules. Such rules may include rules for selecting network content, types of nodes, and the like. The network modeling engine 112 may select one or more data sets from experimental data database 106, including a combination of in vitro and in vivo experimental results. The network modeling engine 112 may utilize the experimental data to verify nodes and edges identified in the literature. In the example of modeling cellular stress, the network modeling engine 112 may select data sets for experiments based on how well the experiment represented physiologically-relevant stress in non-diseased lung or cardiovascular tissue. The selection of data sets may be based on the availability of phenotypic stress endpoint data, the statistical rigor of the gene expression profiling experiments, and the relevance of the experimental context to normal non-diseased lung or cardiovascular biology, for example.

After identifying a collection of relevant networks, the network modeling engine 112 may further process and refine those networks. For example, in some implementations, multiple biological entities and their connections may be grouped and represented by a new node or nodes (e.g., using clustering or other techniques).

The network modeling engine 112 may further include descriptive information regarding the nodes and edges in the identified networks. As discussed above, a node may be described by its associated biological entity, an indication of whether or not the associated biological entity is a measurable quantity, or any other descriptor of the biological entity, while an edge may be described by the type of relationship it represents (e.g., a causal relationship such as an up-regulation or a down-regulation, a correlation, a conditional dependence or independence), the strength of that relationship, or a statistical confidence in the relationship, for example. In some implementations, for each treatment, each node that represents a measureable entity is associated with an expected direction of activity change (i.e., an increase or decrease) in response to the treatment. For example, when a bronchial epithelial cell is exposed to an agent such as tumor necrosis factor (TNF), the activity of a particular gene may increase. This increase may arise because of a direct regulatory relationship known from the literature (and represented in one of the networks identified by network modeling engine 112) or by tracing a number of regulation relationships (e.g., autocrine signaling) through edges of one or more of the networks identified by network modeling engine 112. In some cases, the network modeling engine 112 may identify an expected direction of change, in response to a particular perturbation, for each of the measurable entities. When different pathways in the network indicate contradictory expected directions of change for a particular entity, the two pathways may be examined in more detail to determine the net direction of change, or measurements of that particular entity may be discarded. The computational network models may be generated by the system 100, imported into the system 100, or identified within the system 100 (e.g., from a database of biological knowledge).

Returning to FIG. 2, at step 216, the network scoring engine 114 generates network response scores for each perturbation using the networks identified at step 214 by the network modeling engine 112 and the data received in the form of SRPs generated at step 212 by the SRP engine 110. A network response score quantifies a biological response to a treatment (represented by the SRPs) in the context of the underlying relationships between the biological entities (represented by the identified networks). These network response scores may represent numerically or graphically the effect of perturbing a biological system, for example, by exposing to a potentially harmful agent. By providing a measure of network response to the treatment, these network response scores may allow correlation of molecular events (as measured by experimental data) with phenotypes that characterize the network at the cell, tissue, or organ level. The network scoring engine 114 may include hardware and software components for generating network response scores for each of the networks contained in or identified by the network modeling engine 112.

The network scoring engine 114 may be configured to implement a described technique that generates scalar-valued scores indicative of the overall strength of the response of a network to the treatment, such as a strength scoring technique. A strength score is a mean of the activity observations for different entities represented in the SRP. In some implementations, the strength of a network response is calculated in accordance with:

$$\text{strength} = \frac{\sum_i d_i \beta_i}{NumMeasNodes}$$

where $d_i$ represents the expected direction of activity change for the entity associated with node i, $\beta_i$ represents the log of the fold-change (i.e. the number describing how much a quantity changes going from initial to final value) of activity between the treatment and control conditions, and Num- MeasNodes is the number of nodes with associated measured biological entities. A positive strength score indicates that the SRP is matched to the expected activity change derived from the identified networks, while a negative strength score indicates that the SRP is unmatched to the expected activity change.

The network scoring engine 114 may generate vector-valued scores in addition to or instead of the scalar-valued network scores described above. Examples of methods for calculating a value representing the response of a network, such as geometric perturbation index (GPI), probabilistic perturbation index (PPI) and expected perturbation index (EPI), are described in U.S. provisional application No. 61/525,700, filed Aug. 19, 2011, which is incorporated herein by reference in its entirety. One vector-valued score is the vector of fold-changes or absolute changes in activity for each of the measured nodes. As described above, a fold-change is a number describing how much a measurable changes going from an initial value to a final value under different conditions, such as between the perturbation and control conditions. This fold-change vector has N components, corresponding to the number of nodes in the network with associated measured biological entities. In certain implementations, geometric perturbation index (GPI) values are used in the methods of the present disclosure. In some implementations of calculating a GPI, the ith component of the fold-change vector, $\beta_i$, represents the logarithm (e.g., base 2) of the fold-change of the activity of the ith measured biological entity between the perturbation and control conditions (i.e. the log of the factor by which the activity of the entity changes between the two conditions). In other implementations, other linear or non-linear function can replace the logarithmic function. A weight vector r is also included in calculating a GPI. The weight vector r also has N components, wherein each of the components $r_i$ of the weight vector r represents a weight to be given to the ith observed fold-change $\beta_i$. In some implementations, the weight represents the known biological significance of the ith measured entity with regard to a feature or an outcome of interest (e.g., a known carcinogen in cancer studies). One value that may be advantageously used for weighting is the local false non-discovery rate $fndr_i$ (i.e., the probability that a fold-change value $\beta_i$ represents a departure from the underlying null hypothesis of a zero fold-change, in some cases, conditionally on the observed p-value) as described by Strimmer et al. in "A general modular framework for gene set enrichment analysis," BMC Bioinformatics 10:47, 2009 and by Strimmer in "A unified approach to false discover rate estimation," BMC Bioinformatics 9:303, 2008, each of which is incorporated by reference herein in its entirety. Another weighing factor used for calculating a GPI is the expected directions of change for each component in the fold-change vector $\beta$. The network scoring engine may generate this value by querying the network modeling engine to retrieve the expected directions of change from the causal biological network models. The network scoring engine can then assemble these expected directions of change into an N-component vector d, where the ith component of the vector d, $d_i$, represents the expected direction of change (e.g., +1 for increased activity and −1 for decreased activity) for the ith measured biological entity. In some implementations, this combination is an arithmetic combination, wherein each of the scaled fold-changes $r_i \beta_i$ are multiplied by its corresponding expected direction of change $d_i$ and the result summed over all N biological entities. Mathematically, this implementation can be represented by $$\sum_i d_i r_i \beta_i$$

In other implementations, the vectors d, r and $\beta$ may be combined in any linear or non-linear manner. The combination is normalized by multiplying by a pre-determined scale factor. One such scale factor is the square root of N, the number of biological entities. In this implementation, the GPI score can be represented by:

$$GPI = \frac{\sum_i d_i r_i \beta_i}{\sqrt{N}}$$

In certain implementations, probabilistic perturbation index (PPI) values are used in the methods of the present disclosure. PPI is calculated by combining a positive activation metric $PPI^+$ and the negative activation metric $PPI^-$, for example by:

$$PPI = \tfrac{1}{2}(PPI^+ + PPI^-)$$

The activation metrics are based on a quantification of the probability that the biological mechanisms represented by the networks of interest are activated given the observed system response profile. As for calculating GPI, a fold-change vector $\beta$ is assembled and a fold-change density is generated with a range that represents an approximation of the set of values that the fold-change values can take in the biological system under the treatment conditions, and may be approximated by the range [−W, W], where W is the theoretical expected largest absolute value of a log 2 fold-change. A positive activation metric represents the degree to which the SRPs indicate that the observed activation/inhibition of biological entities is consistent with the expected directions of change represented by the $d_i$. Behavior of the network consistent with a SRP is referred to as positive activation herein and a positive activation metric that may be used is the probability that a network or networks is positively activated, i.e., PPI+, which may be calculated in accordance with the following expression:

$$PPI^+ = Pr(PositivelyActivated) = \frac{1}{W} \int_0^W Pr(PositivelyActivated \mid \varphi) d\varphi$$

in which:

$$Pr(PositivelyActivated \mid \varphi) = \frac{1}{N} \sum_{0 < d_i \beta_i < \varphi} fndr_i$$

where fndri is the false non-discovery rate discussed above. An approximation to the positive activation metric $PPI^+$ can be calculated as follow:

$$PPI^+ \approx \frac{1}{WN} \sum_{0 < d_i \beta_i} fndr_i d_i \beta_i$$

Inconsistent behavior is referred to as negative activation herein. One negative activation metric that may be used is the probability that a network or networks is negative activated. Such a probability, referred to as PPI⁻, may be calculated in accordance with the following expression:

$$PPI^- = Pr(NegativelyActivated) = \frac{1}{W}\int_{-W}^{0} Pr(NegativelyActivated \mid \varphi) d\varphi$$

in which:

$$Pr(NegativelyActivated \mid \varphi) = \frac{1}{N}\sum_{\varphi < d_i\beta_i < 0} fndr_i$$

An approximation to the negative activation metric PPI⁻ can be calculated according to $$PPI^- \approx \frac{1}{WN}\sum_{d_i\beta_i < 0} fndr_i d_i \beta_i$$

Another approach to calculate a value representing network response is the Expected Perturbation Index (EPI) scoring technique. As each SRP represents the activity (or change in activity) of a measured biological entity under a treatment condition, then each SRP is associated with a number of measured activities, one for each measured biological entity. The EPI is a quantification of the average activity change over all biological entities represented by the SRP. Generally the measured activities represented in an SRP may be random draws from a distribution of measured activities, with the EPI representing the expected value of that distribution. If each of the fold-changes $\beta_i$ is drawn from a distribution $p(\cdot)$, then the expected value of that distribution is $$EPI = \int \varphi \cdot p(\varphi) \cdot d\varphi$$

Since the true theoretical distribution $p(\cdot)$ is not readily known, the EPI value may be approximated by using the observed activities and generate an approximate fold-change density. If each of the fold-changes $\beta_i$ drawn from a distribution $p(\cdot)$, then the distribution $p(\cdot)$ can be approximately represented by:

$$\hat{p}(\varphi) \propto \begin{cases} \frac{1}{N}\sum_{i \mid d_i\beta_i > \varphi} \frac{|\beta_i|}{W}, & \varphi > \varepsilon \\ \frac{1}{N}\sum_{i \mid d_i\beta_i < \varphi} \frac{|\beta_i|}{W}, & \varphi < \varepsilon \end{cases}.$$

In some implementations, the network scoring engine 114 applies a computational interpolation technique (e.g., linear or non-linear interpolation techniques) to generate an approximate continuous distribution from the distribution of the above equation, then calculates the expected value of that distribution. In other implementations, the network scoring engine is configured to use the discrete distribution as a rectangular approximation to the continuous distribution, and calculate the EPI in accordance with:

$$EPI \approx \frac{1}{WN}\left[\sum_{i\mid d_i\beta_i>0}(d\beta)_{(i)}\left(\sum_{j=1}^{n_+}(d\beta)_{(j)}\right)((d\beta)_{(i)}-(d\beta)_{(i-1)}) - \right.$$

-continued
$$\left. \sum_{i\mid d_i\beta_i<0}-(d\beta)_{(i)}\left(\sum_{j=1}^{n_-}-(d\beta)_{(j)}\right)(-(d\beta)_{(i)}-(-(d\beta)_{(i-1)}))\right]$$

In this equation, the (·) subscripts represent the values taken in order from smallest fold-change to largest fold change), $n^+$ is the number of entities whose activity was expected to increase in response to the treatment ($d_i\beta_i>=0$) and n– is the number of entities whose activity was expected to decrease in response to the treatment ($d_i\beta_i<=0$). In the EPI score, high value fold-changes are taken into account more often than lower ones, providing a measure of activity with high specificity.

In certain implementations, for each perturbation (for example, exposure to a known or unknown agent), the network scoring engine 114 may generate multiple network response scores constituting a set of scores for a corresponding perturbation or corresponding treatment. For example, the network scoring engine 114 may generate a network response score for a particular network, a particular dose of the agent, and a particular exposure time. The collection of all such network response scores is sent to the aggregation engine 116.

At step 218, the aggregation engine 116 generates a biological impact factor (BIF) based on a plurality of network response scores generated at step 216 by the network scoring engine 116. The aggregation engine 116 may also use other supplementary information derivable from one or more of the networks to generate a BIF. In certain implementations, the aggregation engine 116 may generate a BIF directly from SRPs corresponding to different biological networks. In certain implementations, BIF values may be used to compare the predicted biological outcomes of exposure to different treatments wherein the different outcomes may be caused by the different mechanisms that are induced by the respective treatment conditions. In certain implementations, a BIF may be viewed as an aggregated measure of the effects of a perturbation on multiple underlying biological networks that may contribute to disease onset or a biological outcome. A number of graph-theoretic computational techniques for generating a BIF have been developed, any of which may be performed by the aggregation engine 116; examples of such techniques are discussed below. In certain embodiments, the scores are vector-value scores. In certain embodiments, the scores are not scalar-value scores. In certain embodiments, the one or more biological impact factors is determined by a linear combination, a linear transformation, or a quadratic form of the aggregated scores of the first and second set of scores. Denote the M computational models provided by the network modeling engine 112 as Net-1, Net-2, . . . , Net-M, where M is greater than or equal to one. To generate a BIF, the aggregation engine 116 may use a graph statistics technique that utilize the statistics or characteristics of some or all of the network models, such as the complete network structure, the number of nodes, the number of edges, the weights of the nodes or edges (if weighted), any other properties of the nodes or edges (e.g., the statistical confidence associated with measurements of the biological entities and relationships represented by the nodes and edges, respectively), any nodes or edges that are repeated in different network models, the confidence in the structure of the network model (e.g., a measurement of how consistently the network structure has been replicated in the literature), or any other data representative of the network models provided by the network modeling engine 112. Some of this data may be obtainable from computation performed by the SRP engine 110 (e.g., statistical confidence estimates for measurements), and may be passed to the aggregation engine 116 via the network modeling engine 112, or passed directly from the SRP engine 110 to the aggregation engine 116.

The aggregation engine 116 also receives, for each treatment and each network model Net-i, a vector $S_i$ of one or more network response scores from the network scoring engine 114. As discussed above, $S_i$ may include one or more scalar-valued scores indicative of the overall strength of the response of Net-i to perturbation by the agent. $S_i$ may also include one or more vector-valued scores indicative of the topological distribution of the response of Net-i to perturbation by the agent. The network response score vectors $S_i$ and $S_j$ associated with different network models Net-i and Net-j, respectively, need not have the same dimension, nor be based on any of the same network response score generation techniques.

Figure 5:
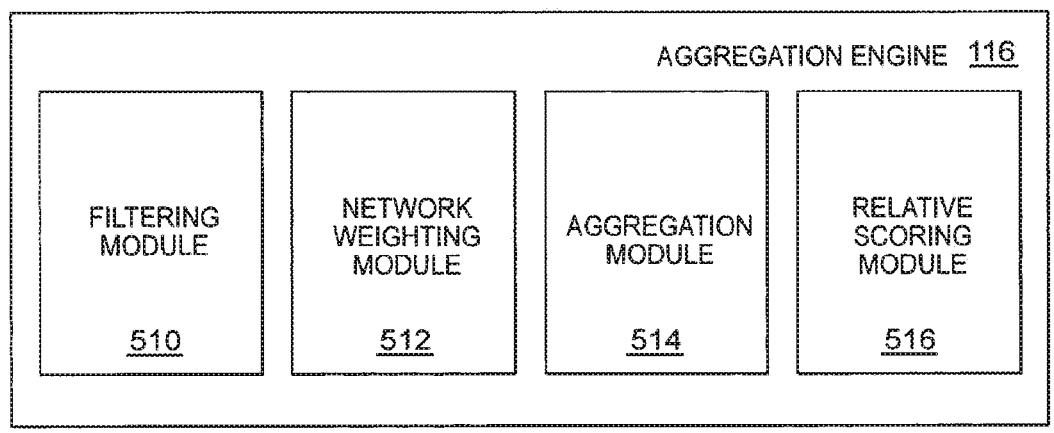
FIG. 5 is a block diagram of an illustrative computerized aggregation engine for generating BIFs.

In certain implementations, the aggregation en gine 116 uses the data from the network modeling engine 112 and the network response scores from the network scoring engine 114 to generate a biological impact factor (BIF). FIG. 5 illustrates four modules that may be included in aggregation engine 116: filtering module 510, network weighting module 512, aggregation module 514, and relative scoring module 516. One or more of these modules 510, 512, 514, 516, may be implemented on at least one of hardware and software, as discussed with reference to FIGS. 11 and 12.

Figure 6:
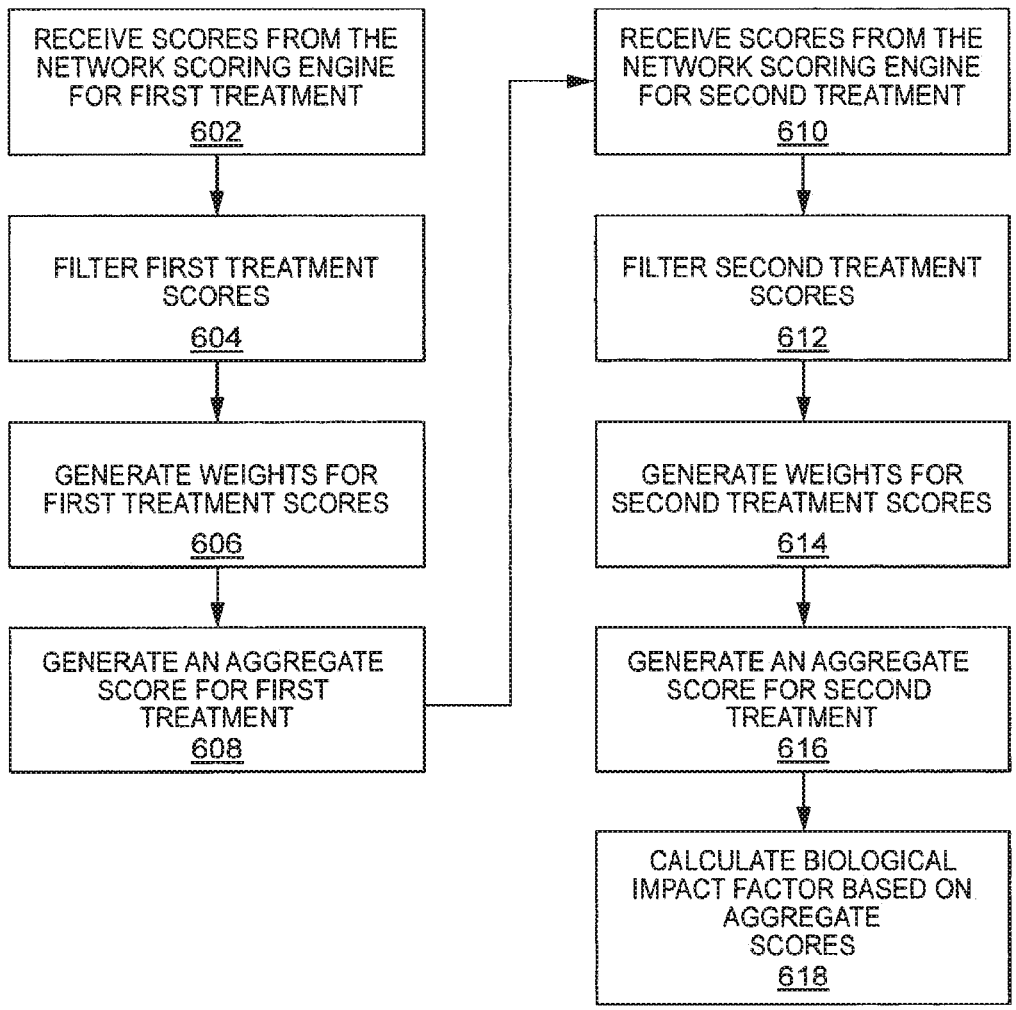
FIG. 6 is a flow diagram of an illustrative process for generating a BIF from network response scores.

The aggregation engine 116 may be configured to generate a BIF according to the illustrative graph-theoretic process 600 depicted in FIG. 6. The steps of the process 600 will now be described as performed by the modules 510-516 (FIG. 5) of the aggregation engine 116, but it will be understood that these steps may be carried out in any suitable order and divided among one or more processing components.

At step 602, the aggregation engine 116 receives information about the computational network models from the network modeling engine 112 and the network response scores from the network scoring engine 114. At step 604, the filtering module 510 filters the score vectors $S_1, S_2, \ldots, S_M$. In some implementations, the filtering operations performed at step 604 include normalizing one or more of the components of one or more of the score vectors. For example, if the first component of each of the score vectors is a scalar-valued score indicative of the overall strength of the response of the associated network model, these first components may be normalized by an appropriate value so that the scores all fall within a desired range. One choice for the appropriate normalizing value is the maximum value of the first component across all score vectors; if all of the first component values re nonnegative, dividing each of the first components by this maximum value will limit the first components to the range [0,1]. In some implementations, the filtering operations performed at step 602 include removing outliers. A component of a score vector may be considered an outlier when its value is more than a designated amount (e.g., a certain number of standard deviations) away from a designated value (e.g., a mean, median or mode). The designated amount and value may be known a priori, or may be computed based on the set of network response score vectors $S_1, S_2, \ldots, S_M$.

Figure 7:
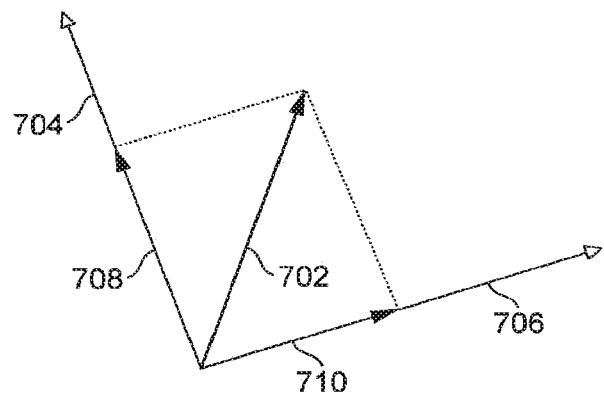
FIG. 7 illustrates an exemplary decomposition of a network response score vector.

In some implementations, the filtering operations performed at step 604 include a geometric graph technique. One such decomposition technique decomposes one or more portions of the score vectors $S_1, S_2, \ldots, S_M$. For illustrative purposes, the decomposition of the entire vector $S_i$ is discussed in the following description, but a decomposition may be performed on only certain components of a score vector. In a decomposition, a vector $S_i$ is written as a combination of two or more other vectors. FIG. 7 illustrates a decomposition of a vector 702 into two components 708 and 710. As is well known in the art, if $S_i$ has dimension p, then $S_i$ can be written as a linear combination of p different basis vectors which span the p-dimensional vector space in which $S_i$ is embedded; in mathematical notation, $$S_i = a_1 v_1 + \ldots | a_p v_p$$

where $\{v_1, \ldots, v_p\}$ is a spanning set of vectors and $\{a_1, \ldots, a_p\}$ are corresponding scalar coefficients. The vector $a_1 v_1$ is referred to as the projection of $S_i$ onto $v_1$. In FIG. 7, vectors 704 and 706 are basis vectors, and the projection of vector 702 onto each of these basis vectors are vectors 708 and 710, respectively. Without loss of generality, $\{v_1, \ldots, v_p\}$ is assumed to be an orthonormal basis. The values of the scalar coefficients can be determined by calculating the inner product between $S_i$ and the corresponding vector.

The aggregation engine 116 may be configured to select (or be pre-programmed with) any of a number of basis vectors $\{v_1, \ldots, v_p\}$. In some implementations, the basis vectors are chosen using the structure of the network model Net-i, for example, using a spectral graph computational technique. Typically, spectral techniques use information derived from an eigen-analysis of a matrix representation of the network model. In one particular spectral technique, the basis vectors $\{v_1, \ldots, v_p\}$ may be the eigenvectors of the combinatorial Laplacian matrix associated with the network model Net-i. If Net-i represents an undirected network with $n_i$ nodes, the combinatorial Laplacian, L, is calculated as $$L = D - A$$

where D is an $n_i$-by-$n_i$ diagonal matrix with the degrees of each node of Net-i on the diagonal and A is the $n_i$-by-$n_i$ node-node adjacency matrix of Net-i. Other matrices whose eigenvectors may provide a suitable basis for a decomposition at step 604 include a node-node adjacency matrix, a node-edge adjacency matrix, a normalized Laplacian matrix, a Gram matrix, or any other matrix representative of the structure of Net-i.

Figure 8A:
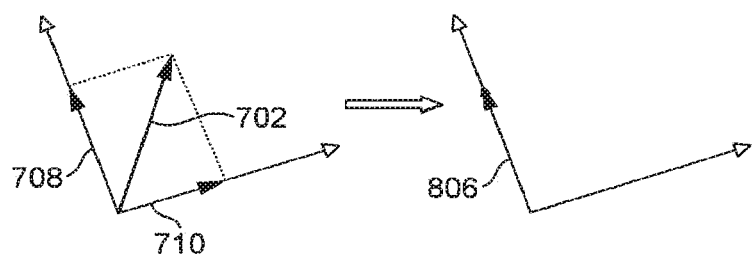
FIGS. 8A and 8B illustrate exemplary filtering operations on a network response score vector.
Figure 8B:
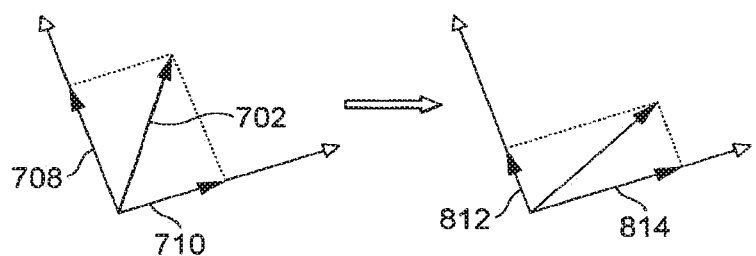

Thus, in one embodiment, each of the scores within the first set and second set of scores includes a score vector, and the step of generating a biological impact factor further comprises filtering, at a processor, the first score and the second score to decompose each of the first and second scores into a plurality of projections onto a set of basis vectors. Filtering may further comprise removing, from at least one of the decomposed first and second scores, at least one of the plurality of projections. The set of basis vectors may comprise the eigenvectors of a matrix descriptive of at least one of the models. In some implementations, the decomposition of $S_i$ may be used to adjust the values of $S_i$, using, for example, a geometric filtering technique or a geometric graph computational technique. In certain aspects, using geometric graph filtering techniques includes modifying geometric representations of one or more network models, such as vector, mesh or higher-dimensional representations. Two such examples are depicted in FIGS. 8A and 8B, respectively. In the first example, the projections of $S_i$ onto some of the basis vectors may be subtracted from $S_i$ ("reducing the dimension" of $S_i$). This is illustrated in FIG. 8A: the vector 702 is decomposed into vectors 708 and 710, and the filtering module 510 removed vector 710 from vector 702, leaving vector 806. The projections that are removed may be those whose magnitude (e.g., length) is smallest. When the basis vectors arose as the eigenvectors of a particular matrix, the projections that are removed may be those associated with eigenvectors whose eigenvalues have the smallest magnitude. A fixed number of projections may be removed or retained. Instead of or in addition to reducing the dimension of $S_i$, each of the projections of $S_i$ may be separately scaled, then the scaled projections added together to form a new score vector $S_i$. This is illustrated in FIG. 8B: the vector 702 is decomposed into vectors 708 and 710, and the filtering module 510 scaled vector 708 to form new vector 812, and scaled vector 710 to form the new vector 814. The scale factors for each of the projections may be chosen in any number of ways, including based on empirical observation or mathematical modeling of the relative significance of each projection. In some implementations, graph spectral information is used. For example, when the basis vectors arose as the eigenvectors of a particular matrix, the scale factors for each projection may be based on the eigenvalues associated with the eigenvectors. For example, the scale value for the projection of $S_i$ onto vector $v_j$ may be given by $$e^{-\lambda_j t}$$

where $\lambda_j$ is the eigenvalue associated with eigenvector $v_j$. The parameter t is tunable, with larger values resulting in smaller scaled projections.

Returning to FIG. 6 at step 604, the network weighting module 512 may weight each of the network response score vectors $S_1, S_2, \ldots, S_M$ associated with each of the M computational models. Generating the first set and second set of scores may comprise: assigning, at a processor, a weight for each of the scores within the first set and second set of scores based on the corresponding computational network model and at least one of the first dataset and the second dataset; aggregating the weighted scores of the first set of scores; aggregating the weighted scores of the second set of scores; wherein the one or more biological impact factor is a function of the aggregated scores of the first set of scores and of the second set of scores. Assigning a weight for each of the scores within the first set and second set of scores comprises selecting a weight for each of the plurality of computational models to maximize the difference between the scores within the first set of scores and the scores within the second set of scores. This weighting may be based on the data received at the step 210 (FIG. 2) and on the corresponding network model. In some implementations, the step 604 includes a graph optimization computational technique. In one such implementation, the weight associated with each score vector is selected in order to maximize the difference between score vectors based on treatment conditions that represent relatively "weak" perturbations to the biological system, and score vectors based on treatment conditions that represent relatively "strong" perturbations to the biological system. FIG. 9 illustrates an example, but in no way limits the range of applications of this approach. FIG. 9 depicts a treatment condition diagram 900 in which a biological system is exposed to a toxic agent for three different exposure times: short 902, medium 904, and long 906. For each exposure time, the SRP engine 110 assembles data representing the measured activity of a set of biological entities. The network modeling engine 112 identifies three different networks Net-1 908, Net-2 910, and Net-3 912, relevant to the toxic agent and the biological system (including the measured biological entities), and the network scoring engine 114 calculates a scalar-valued network response score for each of the three networks and each of the three exposure times. The network weighting module 512 then selects a set of weights, $c_1$, $c_2$ and $c_3$, for the three networks Net-1 908, Net-2 910, and Net-3 912, respectively, so that the weighted sum of the short exposure network response scores are maximally different from the weighted sum of the long exposure network response scores, using the same weights. The weights $c_1$, $c_2$ and $c_3$ may be constrained in some fashion (e.g., $c_1$, $c_2$ and $c_3$ must be nonnegative and must sum to one). In other words, the network weighting module 512 performs the following optimization routine (using any known computational optimization methodology):

$$\max[c_1\|S^1_{LONG} - S^1_{SHORT}\|^2 + c_2\|S^2_{LONG} - S^2_{SHORT}\|^2 + c_3\|S^3_{LONG} - S^3_{SHORT}\|^2]$$
$$\text{s.t.} \ c_1, c_2, c_3 \geq 0$$
$$c_1, +c_2 + c_3 = 1$$

After the weighting of the network response score vectors at step 604 (FIG. 6), the aggregation module 514 combines the network response score vectors separately for each treatment condition at step 606. These vectors may have been filtered by filtering module 510, weighted by network weighting module 512, both, or neither. In some implementations, step 606 includes concatenating all of the network response score vectors for a particular treatment condition into a single vector. Let ASV-i indicate the aggregated score vector for treatment i.

Next, steps 602-606 are repeated for a second treatment condition (represented in FIG. 6 as steps 608-610). These steps may be repeated for as many additional treatment conditions as are of interest, but as discussed above, in some implementations, only two treatment conditions are studied. One of these treatment conditions may include exposure to an agent whose long-term biological effects are reasonably understood (such as smoke from a standard tobacco cigarette), while the second treatment condition may include exposure to an agent whose long-term biological effects are not well understood (such as aerosol or vapor from a tobacco-related product). Regardless of how many treatment conditions are studied, at the conclusion of step 606, an aggregated score vector ASV-i is generated for each treatment condition i.

At step 608, the relative scoring module 516 generates a BIF as a function of the aggregated score vectors. In some implementations, the relative scoring module 516 compares these aggregated score vectors (ASVs) to each other to generate one or more BIFs. As discussed above, a BIF may indicate which biological pathways are similarly activated between different perturbations, which may allow predictions to be made regarding the long-term effects of one perturbation based on the long-term effects of the other perturbation. A number of additional advantages and uses of BIFs are discussed herein. The relative scoring module 516 may generate a BIF from a collection of ASVs in any of a number of ways. In some implementations, step 608 includes a geometric graph technique. For example, a BIF may be generated by computing an inner product between two ASVs, and using the angle associated with that inner product as a BIF measure. In such an implementation, a smaller BIF number indicates greater congruency between the biological mechanisms activated by the two treatment conditions, suggesting similarity in long-term outcomes that depend on those mechanisms. Any of a number of kernels may be used for this inner product computation, including the identity matrix, or a diagonal matrix with various scale factors in the diagonal entries. Some such implementations include graph spectral information. For example, the relative scoring module 516 may use a block diagonal matrix kernel for an inner product calculation, where the ith block is calculated according to:

$$\sum_j e^{-2t\lambda_j} v_j v_j^t$$

where $v_j$ is the jth eigenvector associated with the Laplacian matrix of Net-i and $\lambda_j$ is the associated jth eigenvalue. Using this kernel to compute an inner product between the original score vectors $S_1, S_2, \ldots, S_M$ is an alternative way for aggregation engine 116 to implement the eigenvector decomposition and exponential scaling technique described above with reference to the above equation.

In some implementations, each ASV is used to define a (possibly multi-dimensional) surface, and a BIF is generated by comparing those surfaces. Thus, generating a biological impact factor may comprise determining a distance between at least one first surface defined by at least one first vector representative of the aggregated score of at least one first set of scores and at least one second surface defined by at least one second vector representative of the aggregated second set of scores. Such implementations may include geometric and optimization techniques, among others. Such an approach is illustrated with a simple example in FIG. 10, which is a plot 1000 that depicts surface 1002 corresponding to a first treatment condition and surface 1004 corresponding to a second treatment condition. These surfaces are defined over a dose-exposure time space (dose axis 1008 and time axis 1010), and the height of each surface at a particular dose and exposure time is equal to the value of a scalar network response score 1006 (or scalar-valued aggregation of a vector-valued score or multiple different scores). A BIF can be generated from this surface comparison framework in any of a number of ways. In some implementations, the relative scoring module 516 identifies the dose and time at which the two surfaces are closest to each other. The difference in network response score at this point (i.e., the difference in the heights of the surfaces) represents conditions under which the biological mechanisms activated by one perturbation are closest to those activated by a second perturbation, under the same dose-time conditions. In one example, when the first perturbation is exposure to a known toxic substance, and the second perturbation is exposure to an unknown substance, this minimum distance comparison represents a "worst-case scenario" in which the biological response to the unknown substance is likely to be similar to the biological response of the known toxin. Such worst-case scenarios may be important for research and public health purposes. In some implementations, the relative scoring module 516 identifies the dose and time at which the two surfaces are furthest from each other. Such an implementation may be useful when examining the beneficial properties of a drug or therapy, since the point of maximum difference may illustrate a "worst-case scenario" for the efficacy of a new drug as compared to a well-known, effective drug. In some implementations, the relative scoring module identifies the value of the first surface that is closest to any value of the second surface, regardless of whether those points correspond to the same dose-exposure time conditions. Identifying these closest points may enable useful comparisons to be made between the two perturbations; for example, the effects of perturbations caused by smoking a traditional cigarette for a certain period of time are similar to those caused by inhaling aerosol or vapor from a tobacco-related product for a different period of time.

The relative scoring module 516 may represent the relative scores in a number of different ways. In some implementations, the relative scoring module may output a scalar-valued BIF that summarizes the foregoing experiments and analysis. For example, if the relative scoring module compares the two surfaces of FIG. 10, finds the points at which the values of the two surfaces are most similar, and identifies the corresponding dose and exposure time for the first treatment (dose1 and time1, respectively) and the corresponding dose and exposure time for the second treatment (dose2 and time2, respectively), a scalar-valued BIF may be calculated according to:

$$BIF = \frac{dose1}{dose2} + \frac{time1}{time2}$$

In previous examples, the BIF value is described as relating to a perturbation of a biological mechanism. This BIF value was particularly described, in certain aspects, as a numeric value that quantifies the long-term outcome of that selected perturbation on the respective biological mechanism. However, system 100 is not limited to identifying a BIF for particular perturbations, and instead may be used to generate BIF values for several different perturbations and for predicting several different long-term outcomes of one or more of these perturbations.

Additional and optional to perturbations and outcomes, system 100 may be used to generate one or more BIF values for one or more other parameters including disease outcomes, disease progression, biological mechanisms, and environmental conditions. For example, a plurality of BIF values may be generated, each representing a different level of progression of lung cancer—early stage, metastatic, and late stage. System 100 may include hardware and software components for generating and storing the plurality of BIF values for these different parameters. For example, system 100 may include a database and storage device for storing different BIF values associated with lung cancer progression. Each entry in such a database may include a different BIF value representative of a different stage in the progression of a disease, e.g., lung cancer. The entries in such a database may include additional information associated with the BIF such as a listing of relevant biological mechanisms, and biological entities. The database may be used for several different purposes, e.g., clinical diagnoses and prognoses.

In one example for clinical analysis, system 100 may be used to study the progression of lung cancer in a patient. System 100 may include a database of BIF values representative of different stages in the progression of certain diseases, such as but not limited to lung cancer. In such an example, a patient may have been exposed to a substance having an unknown origin or an unknown identity. The patient may inform a clinician that they were exposed to such a substance which can be a mixture of particulate and gaseous substances that they suspect might potentially impact their health, particularly pulmonary health. The clinician may select one or more assays to perform on biological samples obtained from the patient and generate the measurable data from the patient. In certain implementations, system 100 may assist in the selection of assays. For example, upon the clinician's request for assays informative of the progression of lung cancer, system 100 may display a list of one or more recommended assays to the clinician. The patient's data obtained from one or more assays may be entered into system 100 for computation. Based on the data, system 100 may query the database to obtain entries that have similar experimental results. For example, for gene expression assays, system 100 may query the database to identify entries where genes or gene expression levels match those obtained from the patient's data. In certain implementations, system 100 may filter one or more entries in the database based on other attributes that may not apply to the patient. System 100 may then determine the one or more BIF values that correspond to the selected database entries and attribute these one or more BIF values to the patient. Alternatively, System 100 may use the patient's data to compute a BIF that is specific to the patient and that which can be used to compare with BIF values in the database that represent certain biological outcomes. For example, the database may include BIF values that range from 0 to 100, each value representing a level of progression of lung cancer. In such an example, numbers closer to zero might represent early stage lung cancer, whereas numbers closer to 100 might represent late stage. System 100 may determine that the patient's data produce a BIF value in the range of 10-20, and outputs this result to a display. The clinician or system 100 may interpret this result and inform the patient of their exposure to the substance may be harmful and may represent a certain stage of lung cancer. System 100 may include suitable hardware and software components to receive data, and generate and output BIF values.

Figure 11:
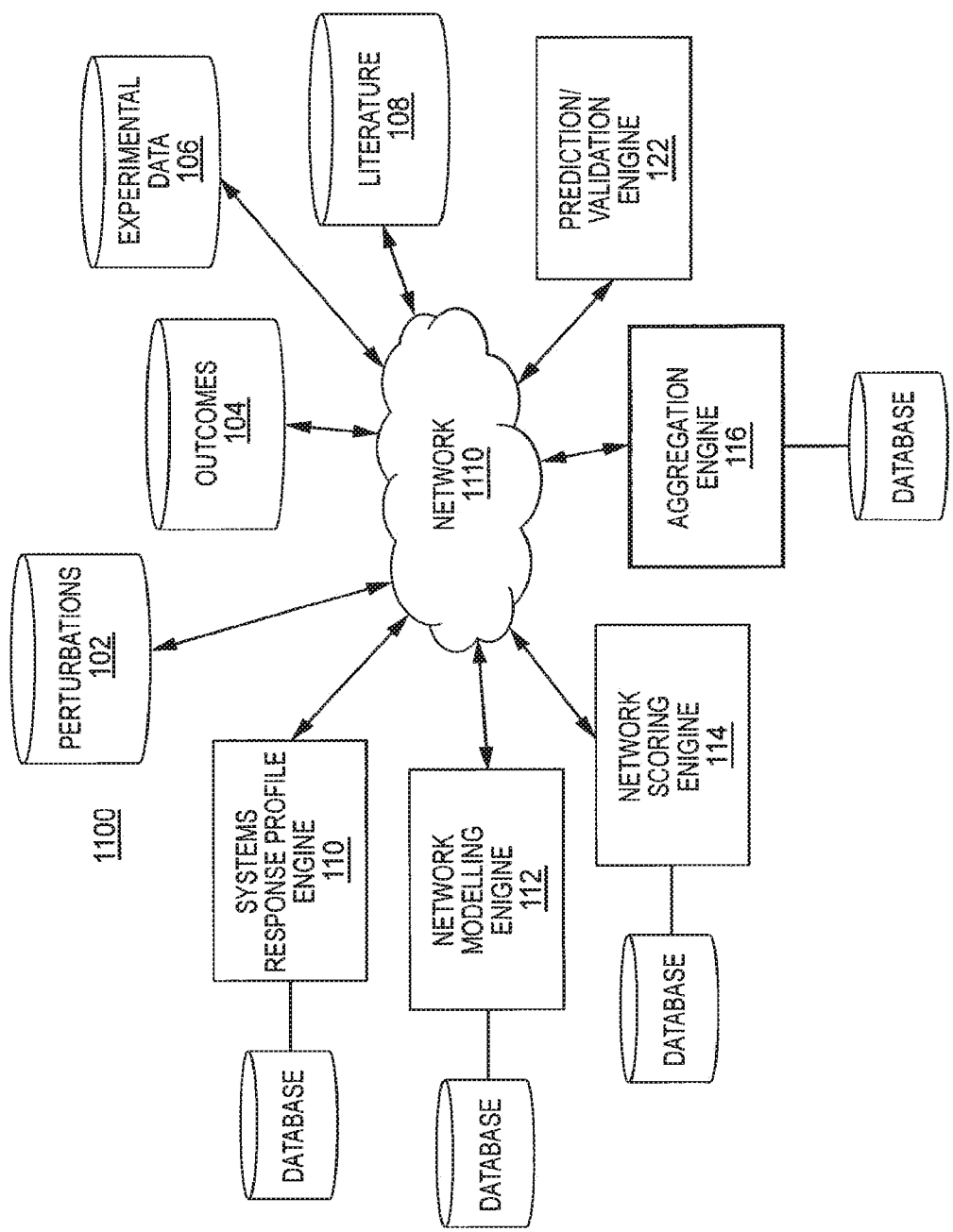
FIG. 11 is a block diagram of an exemplary distributed computerized system for quantifying the impact of biological perturbations.

FIG. 11 is a block diagram of a distributed computerized system 1100 for quantifying the impact of biological perturbations. The components of the system 1100 are the same as those in the system 100 of FIG. 1, but the arrangement of the system 100 is such that each component communicates through a network interface 1110. Such an implementation may be appropriate for distributed computing over multiple communication systems including wireless communication system that may share access to a common network resource, such as "cloud computing" paradigms.

Figure 12:
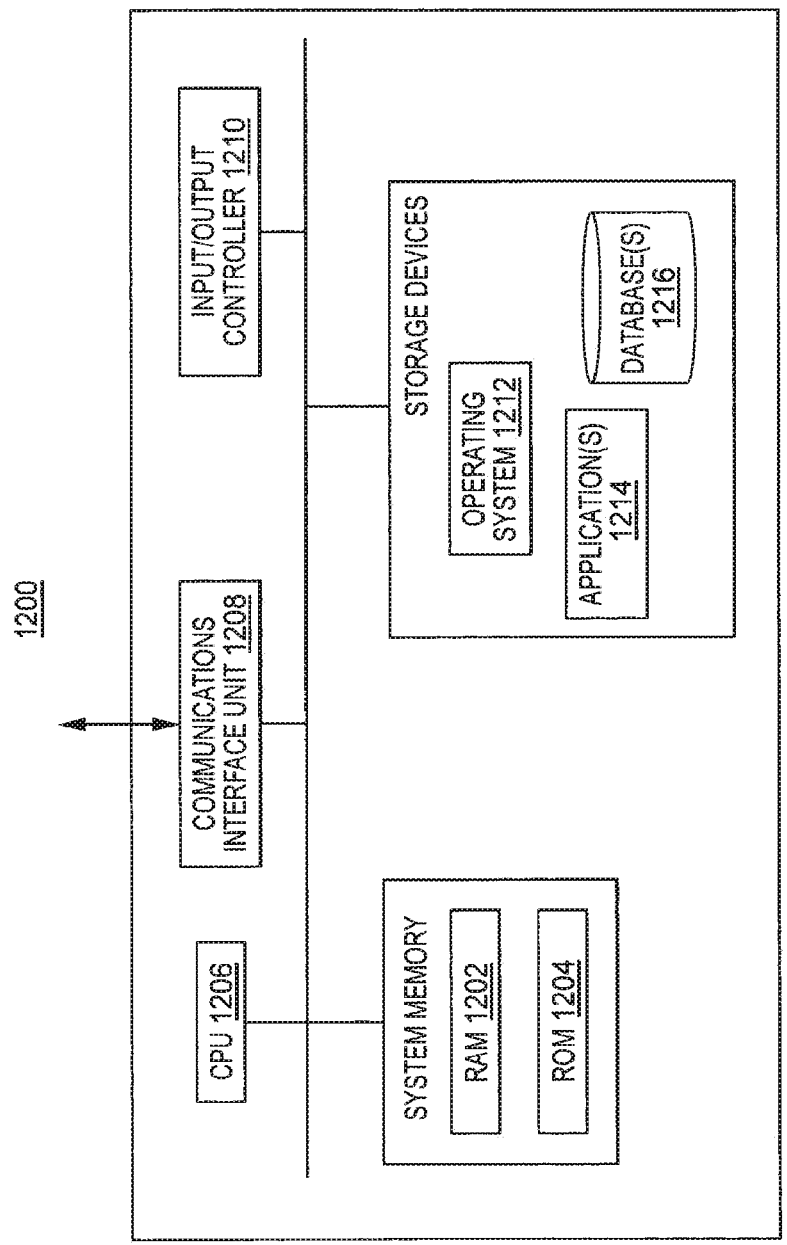
FIG. 12 is a block diagram of an exemplary computing device which may be used to implement any of the components in any of the computerized systems described herein.

FIG. 12 is a block diagram of a computing device, such as any of the components of system 100 of FIG. 1 or system 1100 of FIG. 11 for performing processes described with reference to FIGS. 1-10. Each of the components of system 100, including the SRP engine 110, the network modeling engine 112, the network scoring engine 114, the aggregation engine 116 and one or more of the databases including the outcomes database, the perturbations database, and the literature database may be implemented on one or more computing devices 1200. In certain aspects, a plurality of the above-components and databases may be included within one computing device 1200. In certain implementations, a component and a database may be implemented across several computing devices 1200.

Figure 10:
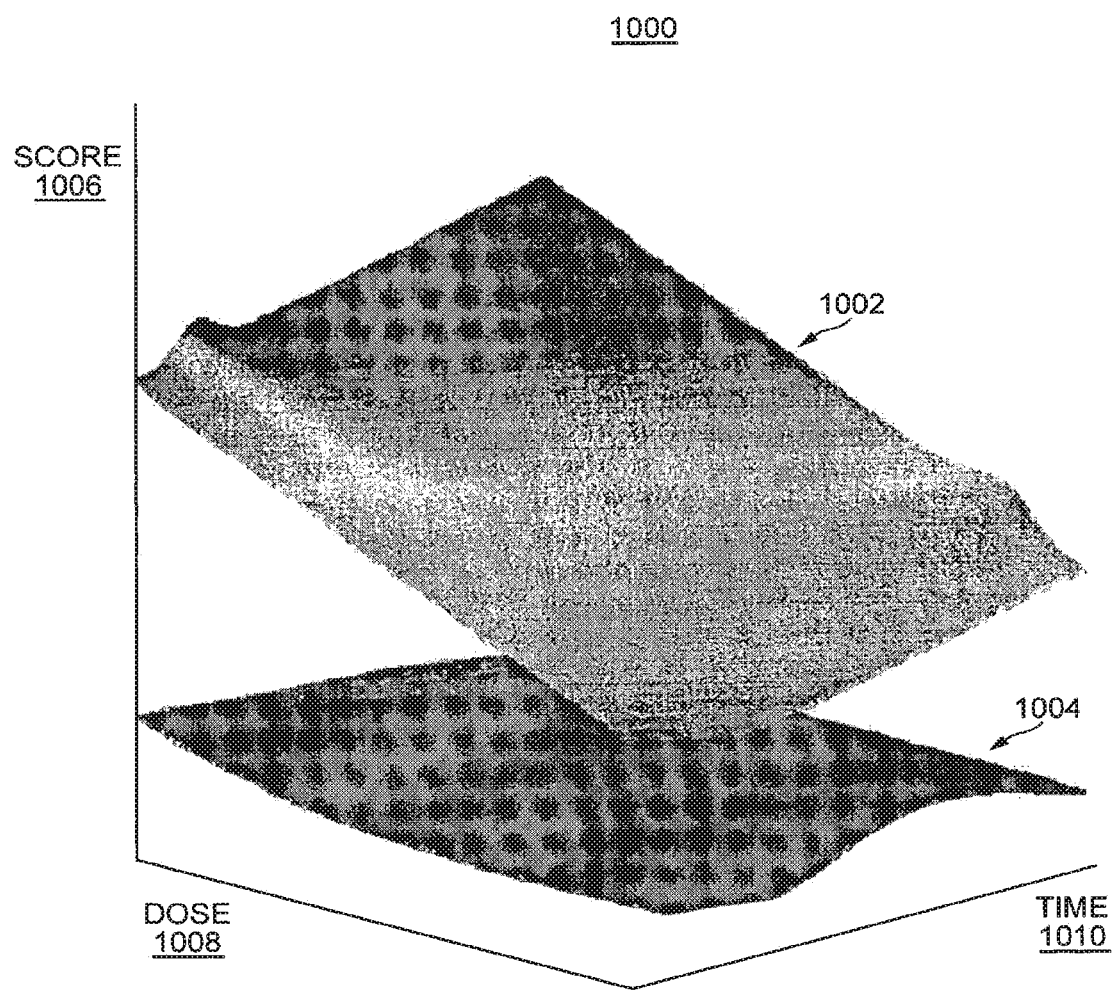
FIG. 10 depicts two network response score surfaces that may be analyzed by the computerized system of FIG. 1.

The computing device 1200 comprises at least one communications interface unit, an input/output controller 1210, system memory, and one or more data storage devices. The system memory includes at least one random access memory (RAM 1202) and at least one read-only memory (ROM 1204). All of these elements are in communication with a central processing unit (CPU 1206) to facilitate the operation of the computing device 1200. The computing device 1200 may be configured in many different ways. For example, the computing device 1200 may be a conventional standalone computer or alternatively, the functions of computing device 1200 may be distributed across multiple computer systems and architectures. The computing device 1200 may be configured to perform some or all of modeling, scoring and aggregating operations. In FIG. 10, the computing device 1200 is linked, via network or local network, to other servers or systems.

The computing device 1200 may be configured in a distributed architecture, wherein databases and processors are housed in separate units or locations. Some such units perform primary processing functions and contain at a minimum a general controller or a processor and a system memory. In such an aspect, each of these units is attached via the communications interface unit 1208 to a communications hub or port (now shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 1206 comprises a processor, such as one or more conventional microprocessors and one or more supplementary co-processors such as math co-processors for offloading workload from the CPU 1206. The CPU 1206 is in communication with the communications interface unit 1208 and the input/output controller 1210, through which the CPU 1206 communicates with other devices such as other servers, user terminals, or devices. The communications interface unit 1208 and the input/output controller 1210 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 1206 is also in communication with the data storage device. The data storage device may comprise an appropriate combination of magnetic, optical or semiconductor memory, and may include, for example, RAM 1202, ROM 1204, flash drive, an optical disc such as a compact disc or a hard disk or drive. The CPU 1206 and the data storage device each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wired medium or combination of the foregoing. For example, the CPU 1206 may be connected to the data storage device via the communications interface unit 1208. The CPU 1206 may be configured to perform one or more particular processing functions.

The data storage device may store, for example, (i) an operating system 1212 for the computing device 1200; (ii) one or more applications 1214 (e.g., computer program code or a computer program product) adapted to direct the CPU 1206 in accordance with the systems and methods described here, and particularly in accordance with the processes described in detail with regard to the CPU 1206; or (iii) database(s) 1216 adapted to store information that may be utilized to store information required by the program. In some aspects, the database(s) includes a database storing experimental data, and published literature models.

The operating system 1212 and applications 1214 may be stored, for example, in a compressed, an uncompiled and an encrypted format, and may include computer program code. The instructions of the program may be read into a main memory of the processor from a computer-readable medium other than the data storage device, such as from the ROM 1204 or from the RAM 1202. While execution of sequences of instructions in the program causes the CPU 1206 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions in relation to modeling, scoring and aggregating as described herein. The program also may include program elements such as an operating system 1212, a database management system and "device drivers" that allow the processor to interface with computer peripheral devices (e.g., a video display, a keyboard, a computer mouse, etc.) via the input/output controller 1210.

The term "computer-readable medium" as used herein refers to any non-transitory medium that provides or participates in providing instructions to the processor of the computing device 1200 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read. Various forms of computer readable media may be involved in carrying one or more sequences of one or more instructions to the CPU 1206 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 1200 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

As discussed, above, the system 100 may be used to construct networks of biological mechanisms to further a systems-level assessment of the biological impact of perturbations. The following paragraphs describe several example networks, each of which may be used to calculate BIF scores for different outcomes related to the underlying mechanisms.

As a first example, the system 100 was used to construct a lung-focused network for cell proliferation. The lung-focused Cell Proliferation Network was constructed using biological expression language (BEL), a computable framework for biological pathway representation developed by Selventa (Cambridge, Mass., USA), enabling its application to the evaluation of cell proliferation based on data obtained by high-throughput means. The Cell Proliferation Network contains 854 nodes, 1598 edges (1017 causal edges and 581 non-causal edges), and was constructed using information from 429 unique PubMed-abstracted literature sources. Several representative network node types include root protein nodes (e.g., CCNE1), modified protein nodes (e.g., RB1 phosphorylated at specific serine residues, and activity nodes (e.g., kinase activity of CDK2 (kaof(CDK2)) and transcriptional activity of RB1 (e.g., taof(RB1))). Causal edges are cause-effect relationships between biological entities, for example the increased kinase activity of CDK2 causally increases phosphorylation of RB1 at serine 373. Non-causal edges connect different forms of a biological entity, such as an mRNA or protein complex, to its base protein(s) (for example, STAT6 phosphorylated at tyrosine (Y) 641 has a non-causal relationship to its root protein node, STAT6) without an implied causal relationship. A cell proliferation network was constructed in a modular fashion in which a core cell cycle submodel is connected to additional biological pathways that contribute to cell proliferation in the lung. Briefly, five submodels are used which include cell cycle (includes canonical elements of the core machinery regulating entry and exit from the mammalian cell cycle, including but not limited to cyclin, CDK, and E2F family members); growth factors (includes common extracellular growth factors involved in regulating lung cell proliferation, namely EGF, TGF-beta, VEGF, and FGF family members); intra- and extracellular signaling (includes elements of the common intra- and extracellular pathways involved in mediating lung cell proliferation, including the Hedgehog, Wnt, and Notch signaling pathways, and calcium signaling, MAPK, Hox, JAK/STAT, mTOR, prostaglandin E2 (PGE2), Clock, and nuclear receptor signaling as relevant to lung cell proliferation); cell interaction (includes the signal transduction pathways leading to cell proliferation that originate from the interactions of common cell adhesion molecules (including ITGB1 complexes with ITGA1-3 chains) and extracellular matrix components (specifically collagen, fibronectin, and laminin)); and epigenetics (includes the main known epigenetic modulators of lung cell proliferation including the histone deacetylase (HDAC) family and DNA methyltransferase (DMT) family member DNMT1).

In order to verify the content of the network, the system 100 was used to analyze transcriptomic data sets using Reverse Causal Reasoning (RCR), which identifies upstream controllers ("hypotheses") that can explain the significant changes in mRNA state in a given transcriptomic data set. Transcriptomic data sets were used to verify and expand the model using public data repositories such as GEO (Gene Expression Omnibus) and ArrayExpress. Data sets used include the EIF4G1 data set (GSE11011), the RHOA data set (GSE5913), the CTNNB1 data set (PMID 15186480), and the NR3C1 data set (E-MEXP-861). The system 100 was used to perform RCR-analysis on each of these four cell proliferation transcriptomic data sets and evaluated the resulting hypotheses. Predictions for many nodes in the core cell cycle block, including a prediction of increased E2F1, 2, and 3 activities, was consistent with their published role in regulating cell proliferation in lung relevant cell types. In addition, predictions for increased MYC activity in the RhoA and CTNNB1 data sets were consistent with the reported role of MYC in positively regulating cell proliferation in lung and lung relevant cell types. In addition to predictions for increased activity of positive cell proliferation mediators in data sets where cell proliferation was experimentally induced to increase, RCR also predicted decreased activities of negative regulators of proliferation. For example, decreases in the transcriptional activity of RB1 and E2F4, both known negative regulators of cell cycle progression, were predicted in multiple data sets. Likewise, decreases in the abundance of CDKN1A or CDKN2A, cell cycle checkpoint proteins with potent anti-proliferative effects, were also predicted in all three data sets where proliferation was observed increased. Many of these hypotheses are pleiotropic signaling molecules, which are involved in other processes in addition to proliferation, and may result from the perturbation of non-proliferative areas of biology in the data sets examined. In addition to verifying the cell proliferation literature model, RCR on the four cell proliferation data sets was used to identify other mechanisms impacting cell proliferation in the lung. For example, the transcriptional activity of Zbtb17 (MIZ-1), was predicted to be increased in the CTNNB1 data set, though Zbtb17 does not yet have a direct literature-described role in regulating normal lung cell proliferation. Accordingly, in certain embodiments, the biological impact of an agent on a mammalian subject, such as a human, can be assessed by analyzing data in at least a network model of lung cell proliferation. Suitably, the lung cell proliferation network model comprises at least one or a combination of two or more of the following submodels: cell cycle, growth factors, intracellular and extracellular signaling, cell interactions, and epigenetics.

As a second example, the system 100 was used to construct a network model of the main pulmonary inflammatory processes (the Inflammatory Process Network, or IPN) by combining a survey of relevant published literature with the computational analysis of multiple transcriptomic data sets. To capture the contribution of multiple cell types to pulmonary inflammation, the system 100 was configured to construct the IPN model using a modular schema, with the larger network model comprised of constituent submodels. The at least 23 scorable IPN submodels focus on the main cell types known to be involved in cigarette smoke-induced pulmonary inflammation; specifically, pulmonary epithelial cells, macrophages, neutrophils, T-cell subsets (Th1, Th2, Th17, Treg, and Tc), NK cells, dendritic cells, megakaryocytes, and mast cells. Within each submodel, an input-output design was used; submodel inputs are signaling ligands/triggers that induce or suppress an intracellular signaling cascade, while submodel outputs are the cellular/physiological products of these signaling pathways (largely secreted cytokines or biological processes). The system 100 was used to construct the IPN model according to the processes described above, including surveying the scientific literature, extracting causal relationships from the Selventa Knowledgebase, receiving manually curated statements from the literature, and adding nodes derived from reverse causal reasoning (RCR) analysis of transcriptomic profiling experiments that assessed specific inflammation-relevant processes. RCR augmentation was based on data sets obtainable from Gene Expression Omnibus (GEO), representing mouse whole lung exposed to LPS in vivo (GSE18341), dendritic cell activation/monocyte-macrophase differentiation/NK cell activation in response to IL15/Th1 differentiation/Th2 differentiation in vitro (GSE22886) and pulmonary neutrophils exposed to LPS in vivo (GSE2322). Accordingly, in certain embodiments, the biological impact of an agent on a mammalian subject, such as a human, can be assessed by analyzing data in at least a network model of lung inflammation. Suitably, the lung inflammation network model comprises at least one or a combination of two or more of the following submodels comprising respectively one or more of the exemplary nodes (in parenthesis): (1) Mucus hypersecretion (hypersecretion and MUCSAC expression in pulmonary epithelial cells in response to cytokines such as IL13, CCL2, TNF, and EGF); (2) Epithelial cell bather defense (changes of epithelial barrier function and tight junction permeability in response to signals such as EGF, TNF, ADAM17, and ROS); (3) Epithelial cell proinflammatory signaling (expression of inflammatory proteins in response to upstream signals, such as TNF, TLR4, ELA2, and IL-1 beta during epitheliel cell activation); (4) Neutrophil response (in response to upstream signals, such as TNF, CSF3, and FPR1); (5) Macrophage-mediated neutrophil recruitment (secretion of IL-8, SERPINE 1, and leukotriene B4 leading to neutrophil chemotaxis and recruitment in response to upstream signals, such as TNF); (6) Neutrophil chemotaxis (regulation of chemotaxis in response to upstream signals, such as CSF3, F2, ILa CXCL12, S100A8, and S100A9); (7) Tissue damage (release of DAMPs and PAMPs as inflammatory triggers following tissue damage leading to TLR and NFkB signaling); (8) Macrophage activation (NFkB-dependent production of proinflammatory molecules in response to upstream signals, such as Toll-like receptor ligation); (9) Macrophage differentiation (differentiation in response to upstream signals, such as IL-6, IGF1, and interferon gamma); (10) Th1 differentiation (Th1 differentiation and IFNG expression in response to upstream signals, such as CCL5 and DLL1); (11) Th1 response (upstream signals, such as IFNG, IL2, LTA, and LTB); (12) Th2 differentiation (in response to upstream signals, such as IL4, IL25, and VIP); (13) Th 17 differentiation (in response to upstream signals, such as TGFB1 and DLL4); (14) Th17 response (in response to upstream signals, such as IL21, IL22, and IL26); (15) Treg response (Regulatory T cell differentiation and IL10 expression in response to upstream signals, such as TGFB1 and IL7); (16) Tc response (Induction of FASLG as a cytotoxic T cell response in response to upstream TCR ligation and IL15); (17) NK cell activation (induction of target cell cytolysis by NK cell response to upstream signals, such as IL-2, IL-4, IL-7, IL-12, IL-15, TGFbeta1, IFNalpha1, and ITGB2); (18) Mast cell activation (in response to upstream signals, such as IL4, KITLG, and FcIgE receptor); (19) Dendritic cell activation (Production of cytokines and other inflammation-related proteins in response to upstream TLR ligands, such as LPS and HMGB1); (20) Dendritic cell migration to tissue (Regulation of migration to site of infection in response to upstream signals, such as complements, CCL3 and CCL5); (21) Dendritic cell migration to lymph node (Regulation of migration to lymph nodes in response to upstream signals, such as CXCL9. CXCL10, CXCL11, CCL19 and CCL21); (22) Th2 response (immune response to upstream signals such as IL-4 and IL-13); and (23) Megakaryocyte differentiation (megakaryocyte differentiation in response to upstream signals, such as IL11 and CXCL12). Accordingly, the computerized methods of the disclosure for determining biological impact can comprise using a network model of pulmonary inflammatory processes which comprises one or more of the 23 submodels.

As a third example, the system 100 was used to build a comprehensive network model that captured the biology underlying the physiological cellular response to endogenous and exogenous stressors in non-diseased mammalian pulmonary and cardiovascular cells. The system 100 was used to construct the cellular stress network (CSN) model according to the processes described above, including surveying the scientific literature, extracting causal relationships from the Selventa Knowledgebase, and receiving manually curated statements from the literature. The CSN model was comprised of six submodels: (1) xenobiotic metabolism response (including AHR, Cytochrone p450 enzymes, and various environmental inducers of this response); (2) endoplasmic reticulum (ER) stress (including the unfolded protein response and the pathways downstream of three stress sensors, Perk (Eik2ak3), ATF6 and Irelalpha (Ern1), while excluding the pro-apoptotic arm of the response); (3) endothelial shear stress (including the effects of laminar (atheroprotective) and turbulent (atherogenic) shear stress on monocyte adhesion, including NF-κB and nitric oxide pathways); (4) hypoxic response (including HIf1α activation and targets, control of transcription, protein synthesis, and crosstalk with oxidative stress, ER stress and osmotic stress response pathways); (5) osmotic stress (includes Nfat5, aquaporin, and Cftr pathways downstream of the hyperosmotic response); and (6) oxidative stress (includes intracellular free radical management pathways, endogenous/exogenous oxidants (including those induced by exposure to hyperoxic conditions) and anti-oxidants, glutathione metabolism, p38, Erk, Jnk, and NF-κB pathways, as well as NRF2 and its upstream regulators and downstream antioxidant response element (ARE)-mediated gene expressions). Accordingly, in certain embodiments, the biological impact of an agent on a mammalian subject, such as a human, can be assessed by analyzing data in at least a network model of cell stress. Suitably, the cell stress network model comprises at least one or a combination of two or more of the following submodels: xenobiotic metabolism response, endoplasmic reticulum (ER) stress, endothelial shear stress, hypoxic response, osmotic stress, and oxidative stress.

The system 100 was used to evaluate the CSN model against a data series representing the transcriptional response to cigarette smoke (CS) as a prototypic induces of pleiotropic cellular stress in mouse lung (GSE18344). The data series included data from both wild type and NRF2 knockout animals exposed to ambient air (sham exposure) or CS, with the 1 day CS treatment data chosen to test the CSN model. Significant mRNA State Changes (SCs) were determined for three comparisons: wild type 1 day CS v. sham exposure, NRF2 knockout 1 day CS v. sham exposure and NRF2 knockout 1 day CS v. wild type 1 day CS exposure. The experimental results were consistent with a central role for NRF2 in the lung cellular response to CS. In particular, 35% of SCs induced by 1 day CS exposure in wild type mice can be explained by activation of NRF2. When the 1 day CS exposed NRF2 knockout mice are compared to the wild type mice, decreased transcriptional activity of NRF2 is predicted, consistent with the absence of NRF2 in these mice. Accordingly, the computerized methods of the present disclosure for determining biological impact can comprise using a network model of cell stress which comprises one or more of the 5 submodels.

As a further example, the system 100 was used to construct a network model for DNA damage response, apoptosis, necroptosis, autophagy and senescence by combining a survey of relevant published literature with the computational analysis of multiple transcriptomic data sets. The network is known as the DACS network for DNA damage, autophagy, cell death and senescence. The DACS Network is constructed using a highly modular design, where the larger network is divided into submodels. Discrete mechanisms affecting cell fate (for example, the prosurvival effects of NFκB-mediated transcriptional upregulation of anti-apoptotic genes) in the five DACS Network areas are described by 35 submodels. In total, the DACS Network contains 1052 unique nodes and 1538 unique edges (959 causal edges and 579 non-causal edges), which are supported by 1231 PubMed-referenced literature citations. Nodes in the DACS Network are biological entities such as protein abundances, mRNA expressions, and protein activities. In addition, nodes can also represent biological processes (e.g., apoptosis). Edges are relationships between the nodes, and are categorized as either causal or non-causal. The DACS Network is constructed and populated with content from two main sources; nodes and edges derived from prior knowledge described in the scientific literature, and nodes obtained from the computational analysis of transcriptomic profiling data via Reverse Causal Reasoning (RCR).

Suitably, the DACS network model comprises at least one or a combination of two or more of the following submodels: for apoptosis—(1) caspase cascade, (2) ER-stress induced apoptosis, (3) MAPK signaling, (4) NFkappaB signaling, (5) PKC signaling, (6) proapoptopic mitochondrial signaling, (7) prosurvival mitochondrial signalling, (8) TNFR/Fas signaling, (9) TP53 transcriptional signature; for autophagy—(10) ATG induction of autophagy, (11) autophagy induction, (12) mTOR signaling, (13) nutrient transporter synthesis and (14) protein synthesis; for DNA damage—(15) components affecting TP53 activity, (16) components affecting TP63 activity, (17) components affecting TP73 activity, (18) DNA damage to G1/S checkpoint, (19) DNA damage to G2/M checkpoint, (20) double stranded break response, (21) inhibition of DNA repair, (22) NER/XP pathway, (23) single stranded break response, (24) TP53 transcriptional signature; for necroptosis—(25) Fas activation, (26) gene signature, (27) proinflammatory mediators, (28) RIPK/ROS mediate execution, (29) TNFR1 activation; for senescence—(30) oncogenes induced senescence, (31) replicative senescence, (32) stress induced premature senescence; (33) regulation of p16INK expression, (34) regulation of tumour suppressors and (35) transcriptional regulation of SASP.

RCR-based augmentation of the DACS Network is performed using four transcriptomic data sets (two for DNA damage and two for senescence), referred to as "building" data sets. Ideally, transcriptomic data sets addressing all five DACS areas are used in order to maximize network coverage. However, because three of the DACS Network areas (apoptosis, autophagy, and necroptosis) have not been classically described as driven by transcriptomic changes, efforts are focused on transcriptomic data from experiments describing the DNA damage response and the induction of senescence. The four building data sets were all derived from in vitro experiments done in human or mouse fibroblasts, and represent the response to DNA damage by ultraviolet irradiation or a chemical DNA crosslinking agent, the induction of replicative senescence by continuous passage, and stress-induced premature senescence (SIPS) induced by bleomycin (GSE13330). Accordingly, in certain embodiments, the biological impact of an agent on a mammalian subject, such as a human, can be assessed by analyzing data in at least a DACS network model. Suitably, the DACS network model comprises at least one or a combination of two or more of the submodels described above.

A plurality of computational causal network models are presented at a processor that represent a biological system, each computational model including nodes representing the plurality of biological entities and edges representing relationships between entities in the plurality of biological entities. In one embodiment, the computational causal network models are selected from two or more of a Cell Proliferation Network, an Inflammatory Process Network, a Cellular Stress Network and a DNA Damage, Autophagy, Cell Death and Senescence Network. Each of the network models may comprise constituent submodels.

In one embodiment, the Cell Proliferation Network is a lung-focused Cell Proliferation Network. Suitably, the submodels are selected from the group consisting of cell cycle (includes canonical elements of the core machinery regulating entry and exit from the mammalian cell cycle, including but not limited to cyclin, CDK, and E2F family members); growth factors (includes common extracellular growth factors involved in regulating lung cell proliferation, namely EGF, TGF-beta, VEGF, and FGF family members); intra- and extracellular signaling (includes elements of the common intra- and extracellular pathways involved in mediating lung cell proliferation, including the Hedgehog, Wnt, and Notch signaling pathways, and calcium signaling, MAPK, Hox, JAK/STAT, mTOR, prostaglandin E2 (PGE2), Clock, and nuclear receptor signaling as relevant to lung cell proliferation); cell interaction (includes the signal transduction pathways leading to cell proliferation that originate from the interactions of common cell adhesion molecules (including ITGB1 complexes with ITGA1-3 chains) and extracellular matrix components (specifically collagen, fibronectin, and laminin)); and epigenetics (includes the main known epigenetic modulators of lung cell proliferation including the histone deacetylase (HDAC) family and DNA methyltransferase (DMT) family member DNMT1), or a combination of two or more thereof.

In one embodiment, the Inflammatory Process Network is a Pulmonary Inflammatory Process Network. Suitably, the submodels focus on the main cell types known to be involved in cigarette smoke-induced pulmonary inflammation. In one embodiment, the submodels are selected from the group consisting of pulmonary epithelial cells, macrophages, neutrophils, T-cell subsets (Th1, Th2, Th17, Treg, and Tc), NK cells, dendritic cells, megakaryocytes, and mast cells, or a combination of two or more thereof.

In one embodiment, the submodels of the Cellular Stress Network are selected from the group consisting of (1) xenobiotic metabolism response (including AHR, Cytochrome p450 enzymes, and various environmental inducers of this response); (2) endoplasmic reticulum (ER) stress (including the unfolded protein response and the pathways downstream of three stress sensors, Perk (Eik2ak3), ATF6 and Ire1alpha (Ern1), while excluding the pro-apoptotic arm of the response); (3) endothelial shear stress (including the effects of laminar (atheroprotective) and turbulent (atherogenic) shear stress on monocyte adhesion, including NF-κB and nitric oxide pathways); (4) hypoxic response (including HIf1α activation and targets, control of transcription, protein synthesis, and crosstalk with oxidative stress, ER stress and osmotic stress response pathways); (5) osmotic stress (includes Nfat5, aquaporin, and Cftr pathways downstream of the hyperosmotic response); and (6) oxidative stress (includes intracellular free radical management pathways, endogenous/exogenous oxidants (including those induced by exposure to hyperoxic conditions) and anti-oxidants, glutathione metabolism, p38, Erk, Jnk, and NF-κB pathways, as well as NRF2 and its upstream regulators and downstream antioxidant response element (ARE)-mediated gene expressions), or a combination of two or more thereof.

In one embodiment of the DACS network model the submodels are selected from the group consisting of: for apoptosis—(1) caspase cascade, (2) ER-stress induced apoptosis, (3) MAPK signaling, (4) NFkappaB signaling, (5) PKC signaling, (6) proapoptopic mitochondrial signaling, (7) prosurvival mitochondrial signalling, (8) TNFR/Fas signaling, (9) TP53 transcriptional signature; for autophagy—(10) ATG induction of autophagy, (11) autophagy induction, (12) mTOR signaling, (13) nutrient transporter synthesis and (14) protein synthesis; for DNA damage—(15) components affecting TP53 activity, (16) components affecting TP63 activity, (17) components affecting TP73 activity, (18) DNA damage to G1/S checkpoint, (19) DNA damage to G2/M checkpoint, (20) double stranded break response, (21) inhibition of DNA repair, (22) NER/XP pathway, (23) single stranded break response, (24) TP53 transcriptional signature; for necroptosis—(25) Fas activation, (26) gene signature for necroptosis, (27) proinflammatory mediators, (28) RIPK/ROS mediate execution, (29) TNFR1 activation; for senescence—(30) oncogenes induced senescence, (31) replicative senescence, (32) stress induced premature senescence; (33) regulation of p16INK expression, (34) regulation of tumour suppressors and (35) transcriptional regulation of SASP, or a combination of two or more thereof.

In accordance with the systems and methods described herein, computational models may be used to represent any and all aspects of the functioning and structure of biological systems and their components. In particular, the systems and methods described herein are configured to quantify the long-term impact of an agent on any and all aspects of the functioning and structure of biological systems and their components. Thus, while the majority of this specification speaks in terms of biochemical data at the physiologic level, computational models may be used to represent interactions at the levels of ions and atoms (e.g., calcium flux, neurotransmission), nucleic acid, protein, and metabolite biochemistry, organelles, subcellular compartments, cells, tissue compartments, tissues, organs, organ systems, individuals, populations, diet, diseased states, clinical trials, epidemiology, predator prey interactions, and parasite-host interactions.

Examples of biological systems in the human context include, but are not limited to, the pulmonary, integument, skeletal, muscular, nervous, endocrine, cardiovascular, immune, circulatory, respiratory, digestive, urinary, and reproductive systems. In one particular example, computational models could be used to represent the functioning and structure of skeletal muscle fibers in the muscular system. In another example, computational models could be used to represent the functioning of neural control of muscle fiber contraction in the skeletal system. In further examples, computational models could be used to represent the functioning and structure of pathways for visceral motor output or the functioning of synaptic communication in neural tissue in the nervous system. In other examples, computational models could be used to represent the functioning and structure of cardiac cycle and control of heart rate in the cardiovascular system. In yet other examples, computational models could be used to represent the functioning and structure of lymphocytes and immune response in the lymphatic system. In other examples, computational models could be used to represent the manifest of symptoms or adverse heath effects and the onset of diseases. In certain embodiments, the computational models of the present disclosure represent diseases, such as cardiovascular diseases, cancer (lung cancer, in particular), chronic obstructive pulmonary disease, asthma and adverse health conditions associated with smoking cigarettes and consumption of other nicotine-containing compositions. Such computational models can be used in the methods of the present disclosure to predict the biological impact of smoking cigarettes and use of nicotine-containing compositions.

Other examples of biological systems include, but are not limited to, epithelial cells, nerve cells, blood cells, connective tissue cells, smooth muscle cells, skeletal muscle cells, fat cells, ovum cells, sperm cells, stem cells, lung cells, brain cells, cardiac cells, laryngeal cells, pharyngeal cells, esophageal cells, stomach cells, kidney cells, liver cells, breast cells, prostate cells, pancreatic cells, testes cells, bladder cells, uterus cells, colon cells, and rectum cells. Examples of cell functions include, but are not limited to, cell division, cell regulation, control of cellular activity by the nucleus, and cell-to-cell signaling, computational models may be used to represent the functioning and structure of cellular components. Examples of cellular components include, but are not limited to, the cytoplasm, cytoskeleton, ribosomes, mitochondria, nucleus, endoplasmic reticulum (ER), Golgi apparatus, and lysosomes.

In certain aspects, computational models may be used to represent the structure, function and synthesis of proteins. In addition, computational models could be used to represent components of proteins, including, but not limited to, amino acid sequence, secondary and tertiary structure, post-translational modification, such as phosphorylation, conformation data. Furthermore, computational models could be used to represent molecules associated with proteins, including, but not limited to, enzymes.

In certain aspects, computational models are used to represent the structure, function and synthesis of nucleic acids. Nucleic acids are not limited to any particular type of nucleic acid and include, but are not limited to, total genome DNA, cDNA RNA, mRNA, tRNA, and rRNA. In certain aspects, computational models from life sciences information are used to represent the structure and function of DNA replication, DNA repair, and DNA recombination. In another aspect of the systems and methods described herein, computational models identify, for example, a single nucleotide polymorphism (SNP), a splice variant, microRNA, double-stranded RNA (dsRNA), small interfering RNA (also known as short interfering RNA or siRNA), RNA interference (RNAi), a chromosome, a chromosomal modification or a silenced gene.

In certain aspects, computational models are used to represent cancer pathways, including, but not limited to, the functioning of oncogenes and tumor suppressor genes. For example, one or more computational models may be used to represent gene expression of the human p53 tumor suppressor gene. In another aspect, computational models may be used to represent the pathways for various types of cancer, including, but not limited to, cancers of the blood (e.g., leukemia), mouth, lips, nasal cavity and sinuses, larynx, pharynx, esophagus, stomach, lung, liver, pancreas, prostate, kidney, testes, bladder, uterus, cervix, colon and rectum.

In certain aspects, computational models are used to represent the pathways for various types of diseases, including, but not limited to, the functioning of molecular mechanisms underlying diseases. Examples of diseases include, but are not limited to, cardiovascular, coronary, pulmonary, respiratory, hematologic, neurological, psychiatric, neuropsychological, neuromuscular, musculoskeletal, ophthalmological, gastrointestinal, genitourinary, endocrinal, dermatologic, inflammatory, metabolic, pathogenic, and infectious diseases.

In certain aspects, computational models identify a product relationship. Examples of such relationships include, but are not limited to, the following: agent X inhibits a specific function of molecule Y; agent X acts as a drug; agent X is in a published patent; agent X is used to treat disease Y; agent X inhibits the activity of entity Y; and agent X activates the ABC activity of entity Y.

In certain aspects, computational models may be used to represent the functioning and structure of infectious agents. Examples of such infectious agents include, but are not limited to, viruses, bacteria, yeasts fungi, or other microorganisms such as parasites. In another aspect, computational models identify a pathogen such as a virus, bacteria, fungus or prion, with relationship connectors representing implications in specific diseases and other characteristics. In other aspects of the present disclosure, computational models identify that a particular measurable entity is a biomarker for a disease state, drug efficacy, or patient stratification, identify the relationship between model organisms, tissues or other biological models of disease, and the relevant disease(s), or an epidemic and its characteristics.

The following examples are provided as an illustration and not as a limitation. Unless otherwise indicated, the present invention employs conventional techniques and methods that are known in the art.

EXAMPLES

Described herein are novel computational methods that derive quantitative biological impact—defined as a Biologic Impact Factor (BIF)—from underlying system-wide data using defined causal biological (for example, molecular) network models as the substrate for data analysis. This approach enables biological impact assessment of active substances at the pharmacological level a priori, and can identify mechanisms of action through the application of causal biological network models. The impact of a specific biological network perturbation caused by a single, or a mixture of, biologically active substance(s) is determined for every described molecular entity in the network, thereby identifying causal mechanistic effects induced by each substance or mixture. As our approach is based on system-wide experimental data, this quantitative method takes into account entire biological systems and thereby many biological networks perturbed by the active substance(s). This enables a quantitative and objective assessment of each molecular entity (or node) in the described biological network(s) to serve—alone or as part of a signature—as a molecular biomarker closely expressing the overall state of perturbation (activation or inhibition compared to control) of every biological network in the system and its correlation with events such as disease onset or progression. Furthermore, our approach enables the quantitative comparison of biological impact across individuals and species at the mechanistic level while gene-level comparisons are confounded by genomic/genetic variations. This capability provides a means to translate between in vivo and in vitro model system biology and human biology.

This approach provides both potential predictive capabilities and explicit listing of all assumptions through deterministic scoring algorithms. This approach may enable application of network pharmacology and systems biology beyond toxicological assessment, and can be applied in areas such as drug development, consumer product testing and environmental impact analysis. One embodiment of the invention which utilises a five-step approach is described in FIG. 2.

Example 1

Design Experiments for Data Production

For research to translate to human systems, data collected from clinical studies is the most applicable. However, due to the challenges in obtaining large human data sets, it is useful to consider non-human models in vivo as well as models based on cellular and organotypical (3D) cultures in vitro that represent key aspects of human disease. Data derived from these systems allow at least some insight into the biological network perturbations caused by substances to be obtained, to identify mechanism-specific biomarkers for use in human studies, and link these mechanisms to the onset of disease for impact assessments.

Figure 14:
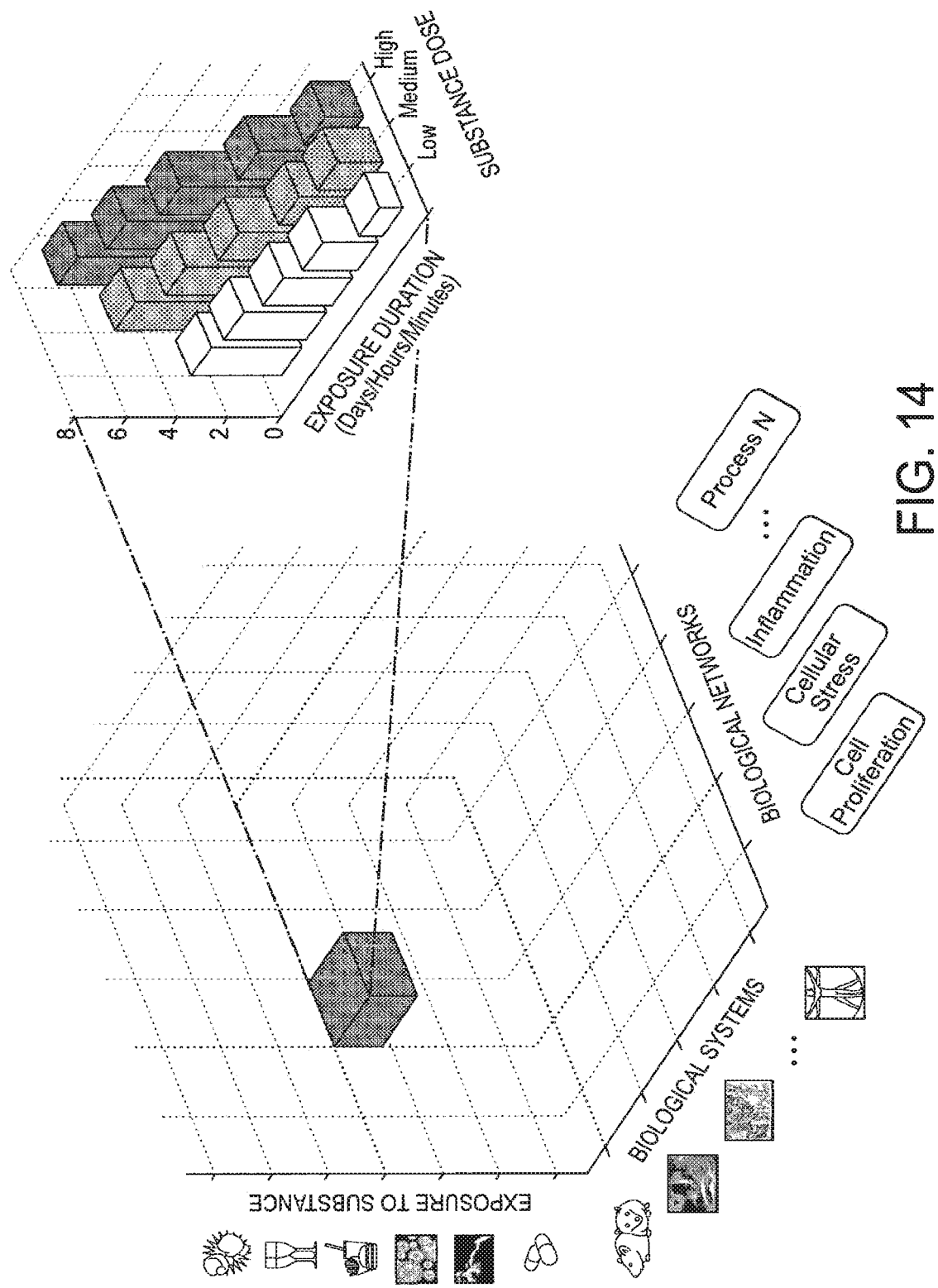
FIG. 14 illustrates a systematic approach to experimental design for biological impact factor assessment. Several well chosen biological systems are exposed to substances in a time and dose dependent manner to generate systems-wide data which will be interpreted in the context of each biological network that is relevant to disease onset.

While experimental systems in vitro and in vivo are known to have many shortcomings, a systematic approach to their use will minimize these issues (FIG. 14). Such a systematic approach may include consideration of a number of constraints:

Exposure. The exposure regimen for a substance or complex stimulus reflects the range and circumstances of exposure in everyday settings. A set of standard exposure regimens is defined to be applied systematically to equally well-defined experimental systems. Furthermore, each assay can be designed to collect time and dose-dependent data to capture both early and late events and ensure a representative dose range is covered.

Experimental Systems. Experimental systems, if possible, can cover two complementary purposes: 1) animal models that reproduce defined features of the human disease and are adequate for the exposure, 2) cellular and organotypical systems selected to reflect the cell types and tissue involved in the disease etiology and priority is given to primary cells or organ cultures that recapitulate as much as possible the human biology in vivo. It is also crucial to match each human culture in vitro with the most equivalent culture derived from the animal models in vivo. This enables creation of a "translational continuum" from animal model to human biology in vivo using the matched systems in vitro as "hubs".

Measurements. High-throughput system-wide measurements for gene expression, protein expression, post translational modifications—such as phosphorylation and metabolite profiles—are generated and correlated with functional outcomes of system exposure. Functional outcome measurements are useful to the strategy as they serve as anchors for the assessment and represent clear steps in the disease etiology. Although animal models and cellular systems do not always completely translate to human disease, some of the steps can be reproduced and these represent a major asset in understanding how biological network perturbations can lead to disease.

Example 2

Computer Systems Response Profiles

The quality controlled measurements generated in the first step constitute a Systems Response Profile (SRP) for each given exposure in a given experimental system. The SRP therefore expresses the degree to which each individual molecular entity is changed as a consequence of the exposure of the system and may be the result of rigorous quality controls and statistical analysis. In this way, different measurements and data types can be integrated and co-analyzed to provide a more accurate quantitative representation of the biology.

Next, measurable elements (e.g., mRNA expression) are causally integrated into biological network models through the use of prior knowledge. This, coupled with the computational methods in development, enables mechanistic assessment and understanding of biological network perturbations caused by active substances.

Example 3

Build Biological Network Models

While the SRPs derived in the previous step represent the experimental data from which biological impact is determined, it is the causal biological network models that are the substrate for SRP analysis. Application of this strategy requires development of detailed causal network models of mechanistic biological processes relevant to risk assessment. Such a framework provides a layer of mechanistic understanding beyond examination of gene lists that have been used in more classical toxicogenomics. A strategy to build such models is developed using BEL (Biological Expression Language), Selventa's computable framework for biological network representation, enabling its application to the evaluation of the biological process of interest based on high-throughput data.

Construction of such a network is an iterative process. Selection of biological boundaries of the network is guided by literature investigation of signaling pathways relevant to the process of interest (e.g., cell proliferation in the lung). Causal relationships describing these pathways are extracted from Selventa's Knowledgebase to nucleate the network with those relationships derived from relevant cell types. The literature-based network can be verified using high-throughput data sets with available phenotypic endpoints.

An example would be microarray analysis of human bronchial epithelial cells perturbed with an inhibitor of the key cell cycle regulator CDK1 in conjunction with proliferation assays. These data sets are analyzed using Reverse Causal Reasoning (RCR), a method for identifying predictions of the activity states of biological entities (nodes in the network) that are statistically significant and consistent with the measurements taken for a given high-throughput data set. RCR prediction of literature network nodes consistent with the observations of cell proliferation in experiments used to generate the high-throughput data verify the network is competent to capture mechanisms regulating the biological process being represented. Additionally, network-relevant nodes predicted by RCR, which are not already represented in the literature network, are integrated. This approach generates a comprehensive biological network with nodes and edges (directional connections between nodes) derived from literature as well as nodes derived from relevant high-throughput data sets.

These networks contain features that may enable process scoring. Topology is maintained; networks of causal relationships (signaling pathways) can be traced from any point in the network to a measurable entity. Further, the models are dynamic and the assumptions used to build them can be modified or restated and enable adaptability to different tissue contexts and species. This allows for iterative testing and improvement as new knowledge becomes available.

Example 4

Compute NPA Scores for Biological Networks from SRPs

To enable a quantitative comparison of the perturbation of biological networks, a computational approach is developed that translates SRPs into network response scores. Network response scores are applied to experimental data within the context of a causal model of a biological network. Specifically, measurements that are causally mapped as downstream effects of perturbation to individual elements in the model are aggregated via techniques described herein into a biological network-specific score. By providing a measure of biological network perturbation, network response scores allow correlation of molecular events with phenotypes that characterize the network at the cell, tissue, or organ level.

Example 5

Computing Biological Impact Factors for Biological Systems

Figure 15:
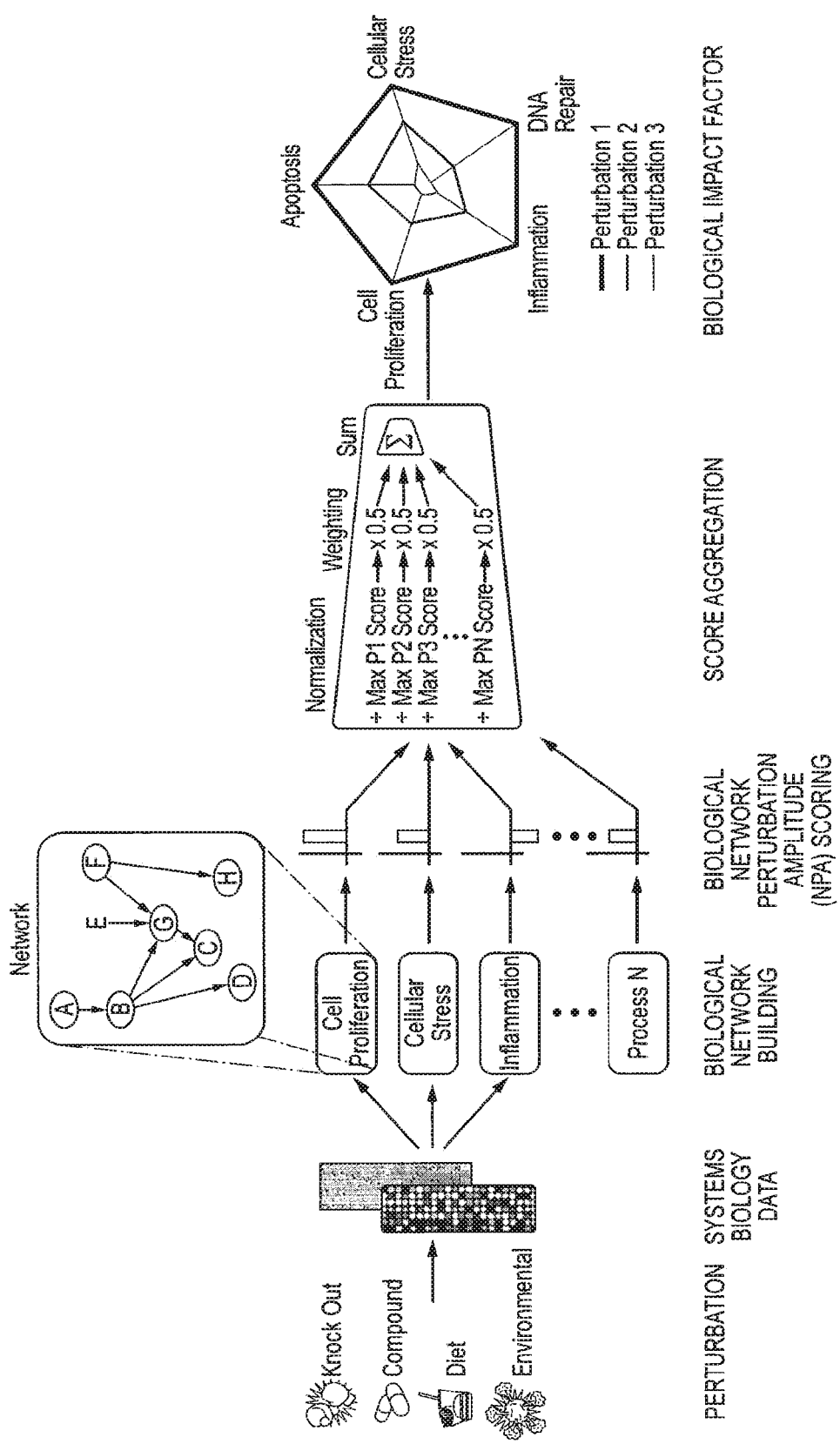
FIG. 15 illustrates a computational process to derive a Biological Impact Factor for a given biologically active substance using systems-wide experimental data analyzed in the context of biological networks linked to disease onset.

A single numerical score can be computed that represents the systems-wide and pan-mechanistic biological impact of a given substance of mixture. Another step in estimating the biological impact of a perturbing agent is to aggregate the network response scores—that express the impact on each individual biological network-into one holistic value that expresses the overall impact on the entire biological system. Network response scores for each contributing network are aggregated to produce an estimate of biological impact in a process that requires both normalizing the scores between networks and weighting the contribution of each network (FIG. 15). The design of the aggregation algorithm may thus address the issue of defining the relative contribution of each biological network to the overall state of the system. Finally, when a BIF is used as a predictor for medium and long term disease outcome, it can be calibrated using a combination of experimental and if available epidemiological data.

Example 6

Figure 13:
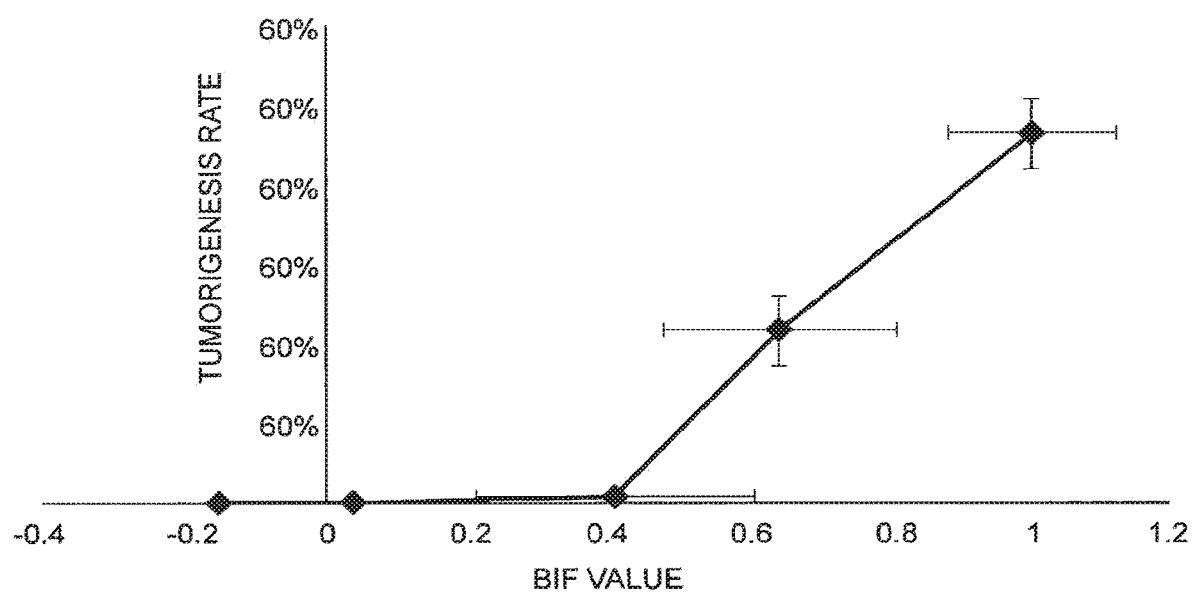
FIG. 13 depicts experimental results for a nasal epithelium tumorigenesis BIF generated according to an illustrative embodiment of the systems and methods disclosed herein.

Quantifying the Impact of Inhaled Chemical Products on Nasal Epithelium Tumorigenesis in Rats As an example of the application of the graph-theoretic BIF techniques disclosed herein, the system 100 was configured to generate a biological impact factor (BIF) to quantify the impact of inhaled chemical products on nasal epithelium tumorigenesis in rats using cell proliferation and inflammation networks. Data derived from the gene expression microarray analysis of rat nasal tissue with time and dose following formaldehyde inhalation is publicly available under Accession Number GSE23179 (Gene Expression Omnibus). To obtain this dataset, eight week old male F344/Cr1BR rats were exposed to formaldehyde through whole body inhalation. Whole-body exposures were performed at doses of 0, 0.7, 2, 6, 10, and 15 ppm (6 hours per day, 5 days per week). Inhalation animals were sacrificed at 1, 4, and 13 weeks following initiation of exposure. Following sacrifice, tissue from the Level II region of the nose was dissected and digested with a mixture of proteases to remove the epithelial cells. The epithelial cells acquired from this section of the nose consisted primarily of transitional epithelium with some respiratory epithelium. Gene expression microarray analysis was performed on the epithelial cells. The systems response profile engine 110 received transcriptomic data from rats exposed for 13 weeks to various doses of formaldehyde, and assembled this data into a systems response profile (SRP). The network modeling engine 112 identified two networks that are associated with tumorigenesis: a proliferation network and an inflammation network. For each dose, the network scoring engine 114 evaluated the proliferation and inflammation networks (and in particular, the transcriptomic behavior predicted by those networks) against the SRP, and calculated network response scores for each of the two networks. Next, the aggregation engine 116 generated a BIF for each dose by averaging the two network response scores (reflecting an assumption that the mechanisms underlying both networks contribute equally to the outcome of interest, i.e., tumorigenesis). The prediction/validation engine 122 then compared the BIF values for each dose against a dose-specific tumorigenesis rate taken from the biological literature. This comparison is depicted in FIG. 13. The results depicted in FIG. 13 indicate that tumorigenesis as predicted by the BIF becomes significant over a threshold BIF of 0.4. In some embodiments, the BIF is calibrated against a known or otherwise predicted biological outcome (as represented in FIG. 13). In other embodiments, the BIF is not calibrated, but BIF values are compared to each other to rank and compare biological outcomes. Initially, the scores were calculated using a strength algorithm and then later confirmed using a geometric perturbation index scoring technique.

Although the present disclosure has been described herein with reference to specific embodiments, it should be understood by those skilled in the art that various changes in form and detail may be made therein without departing from the spirit and scope of the present disclosure. In accordance with the present disclosure, computational models may be used to represent any life-science information. Further aspects of the present disclosure are set forth in the following passages:

1. A computerized method for determining the biological impact of an agent on a biological system, comprising: receiving, at a network modeling engine, data corresponding to a response of a biological system to an agent, wherein the biological system includes a plurality of biological entities, each biological entity interacting with at least one other of the biological entities; receiving, at the network modeling engine, data corresponding to the biological system generating, at the network modeling engine, a plurality of computational models of portions of the biological system; wherein each computational model includes nodes representing the biological entities and edges representing relationships between the biological entities; generating, at a network scoring engine, at least one first score representing the impact of the agent on the plurality of computational models, and at least one second score representing the plurality of computational models of the biological system not exposed to the agent; and generating, at an aggregation engine, an aggregated score representing the biological system.

2. The computerized method of passage 1, wherein the data corresponding to the agent comprises data representations that express the degree to which one or more of the biological entities within the biological network are changed as a consequence of the exposure of the biological system to the agent.

3. The computerized method of either of passages 1 or 2, wherein the network modeling engine identifies, based at least in part on the data corresponding to at least one of the first agent and the second agent, biological entities within the biological system exhibiting statistically significant activity in response to the agent.

4. The computerized method of passage 3, wherein the network modeling engine builds one or more of the computational models having nodes corresponding to the identified biological entities, and edges corresponding to a causal connection between one or more of the identified biological entities.

5. The computerized method of any of passage 1-4, wherein one or more of the plurality of computational models comprises one or more directly measurable nodes, and the data corresponding to at least one of the first agent and the second agent includes measurements of one or more biological entities represented by the one or more directly measurable nodes.

6. The computerized method of passage 5, wherein the network scoring engine assigns a score for the one or more computational models having one or more directly measurable nodes based on a numerical value of the measurement of the biological entity corresponding to the respective node.

7. The computerized method of any of passages 1-6, wherein one or more of the plurality of computational models comprises one or more indirectly measurable nodes, and the data corresponding to at least one of the first agent and the second agent includes measurements of one or more biological entities causally linked to the one or more indirectly measurable nodes.

8. The computerized method of passage 7, wherein the network scoring engine assigns a score for the one or more computational models having one or more indirectly measurable nodes based on a numerical value of the measurement of the biological entity causally linked to the respective node.

9. The computerized method of passage 7, wherein the network scoring engine assigns a score for the one or more computational models having one or more indirectly measurable nodes based on a combined value of the measurements of the biological entities causally linked to the respective node.

10. The computerized method of any of passages 1-9, further comprising: assigning, at the aggregation engine, a weight for each of the plurality of computational models based on the impact of the agent on the corresponding computational model; and generating, at the aggregation engine, a first aggregated score and a second aggregated score by combining the first set of scores and the second set of scores, respectively, according to the assigned weights; wherein the relative aggregated score is a function of the second aggregated score relative 11. The computerized method of passage 10, wherein generating a first aggregated score and a second aggregated score comprises applying a geometric graph computational technique.

12. The computerized method of any of passages 10-11, wherein generating a first aggregated score and a second aggregated score comprises applying a spectral graph computational technique.

13. The computerized method of any of passages 10-12, wherein generating a first aggregated score and a second aggregated score comprises applying a graph optimization computational technique.

14. The computerized method of any of passages 1-13, wherein the at least one first score and the at least one second score include vectors, and the step of aggregating further comprises filtering, at the aggregation engine, the at least one first score and the at least one second score to decompose each of the first and second scores into a plurality of basis vectors having a corresponding scalar coefficients.

15. The computerized method of any of passages 1-14, wherein filtering further comprises removing at least one of the plurality of basis vectors having a corresponding scalar coefficient.

16. The computerized method of any of passages 1-15, further comprising filtering, at the aggregation engine, the at least one first score and the at least one second score to remove statistical outlier values.

17. The computerized method of any of passages 1-16, further comprising normalizing, at the aggregation engine, the at least one first score and the at least one second score.

18. The computerized method of any of passages 1-17, further comprising assigning, at the aggregation engine, a weight for each of the plurality of computational models based maximizing the difference between the at least one first score and the at least one second score, and generating, at an aggregation engine, the relative aggregated score based on the assigned weights.

19. A computer system for determining the biological impact of an agent on a biological system, comprising: a network modeling engine, for receiving data corresponding to a response of a biological system to an agent, and data corresponding to the biological system not exposed to the agent; wherein the biological system includes a plurality of biological entities, each biological entity interacting with at least one other of the biological entities; generating a plurality of computational models of portions of a biological system perturbed by a first agent and a second agent; wherein each computational model includes nodes representing one or more biological entities and edges representing relationships between the biological entities; a network scoring engine, for generating at least one first score representing the impact of the agent on the plurality of computational models, and at least one second score representing the plurality of computational models of the biological system not exposed to the agent; and an aggregation engine, generating an aggregated score representing the biological impact of the agent on the biological system.

20. The computer system of passage 19, wherein the aggregation engine further comprises: a filtering module, for filtering the at least one first score and the at least one second score to generate an at least one first filtered score and an at least one second filtered score; a network weighting module, for assigning a weight for each of the plurality of computational models; and a relative scoring module, for generating a relative aggregated score, based on the at least one first filtered score and the at least one second filtered score.

21. A computerized method for determining a score representing an impact of an agent on a biological system, comprising: receiving, at a network modeling engine, data corresponding to a response of a biological system to a first agent, wherein the biological system includes a plurality of biological entities, each biological entity interacting with at least one other of the biological entities; generating, at the network modeling engine, a plurality of computational models of portions of the biological system; wherein each computational model includes nodes representing the biological entities and edges representing relationships between the biological entities; generating, at a network scoring engine, an expected response for each of the nodes of the plurality of computational models; wherein the expected response is based on the exposure to the agent and at least one of the nodes and the edges of the computational model; receiving, at the network scoring engine, the data; and combining, at the network scoring engine, the expected responses and the data to generate a score representative of the performance of the computational model against the data.

22. A computerized method for determining the biological impact of a second agent relative to the biological impact of a first agent, comprising: receiving, at a network modeling engine, data corresponding to a response of a biological system to a first agent, wherein the biological system includes a plurality of biological entities, each biological entity interacting with at least one other of the biological entities; receiving, at the network modeling engine, data corresponding to a response of the generating, at the network modeling engine, a plurality of computational models of portions of the biological system; wherein each computational model includes nodes representing the biological entities and edges representing relationships between the biological entities; generating, at a network scoring engine, at least one first score representing the impact of the first agent on the plurality of computational models, and at least one second score representing the impact of the second agent on the plurality of computational models; and generating, at an aggregation engine, a relative aggregated score representing the biological impact of the second agent relative to the biological impact of the first agent based on the at least one first score and the at least one second score.

23. A computer system for determining the biological impact of a second agent relative to the biological impact of a first agent, comprising: a network modeling engine, for receiving data corresponding to a response of a biological system to a first agent, and data corresponding to a response of the biological system to a second agent; wherein the biological system includes a plurality of biological entities, each biological entity interacting with at least one other of the biological entities; generating a plurality of computational models of portions of a biological system perturbed by a first agent and a second agent; wherein each computational model includes nodes representing one or more biological entities and edges representing relationships between the biological entities; a network scoring engine, for generating at least one first score representing the impact of the first agent on the plurality of computational models, and at least one second score representing the impact of the second agent on the plurality of computational models; and an aggregation engine, generating a relative aggregated score representing the biological impact of the second agent relative to the biological impact of the first agent based on the at least one first score and the at least one second score.

1a. A computerized method for determining the impact of a perturbation on a biological system, comprising:
  receiving, at a processor, first data corresponding to a response of a set of biological entities to a first treatment, wherein a biological system comprises a plurality of biological entities including the set of biological entities and wherein each biological entity in the biological system interacts with at least one other of the biological entities in the biological system;
  receiving, at a processor, second data corresponding to a response of the set of biological entities to a second treatment different from the first treatment;
  providing, at a processor, a plurality of computational causal network models that represent a biological system, each computational model including nodes representing the plurality of biological entities and edges representing relationships between entities in the plurality of biological entities;
  generating, at a processor, a first score representing the perturbation of the biological system based on the first data and the plurality of computational models, and a second score representing the perturbation of the biological system based on the second data and the plurality of computational models; and
  generating, at a processor, a biological impact factor based on the first and second scores that represents the biological impact of the perturbation on the biological system.

2a. The computerized method of passage 1a, wherein each of the first and second scores includes a score vector, and the step of generating a biological impact factor further comprises filtering, at a processor, the first score and the second score to decompose each of the first and second scores into a plurality of projections onto a set of basis vectors, suitably, wherein filtering further comprises removing, from at least one of the decomposed first and second scores, at least one of the plurality of projections.

3a. The computerized method of passage 2a, wherein the set of basis vectors comprise the eigenvectors of a matrix descriptive of at least one of the computational models.

4a. The computerized method of any of passages 1a to 3a, wherein generating the first and second scores comprises: assigning, at a processor, a weight for each of the plurality of computational models based on the corresponding computational model and at least one of the first data and the second data; generating, at a processor, a plurality of first scores corresponding to the plurality of computational models and based on the first data; generating, at a processor, a plurality of second scores corresponding to the plurality of computational models and based on the second data; combining the plurality of first scores according to the assigned weights; combining the plurality of second scores according to the assigned weights; wherein the biological impact factor is a function of the combined plurality of first scores and the combined plurality of second scores.

5a. The computerized method of passage 4a, wherein determining a weight for each of the plurality of computational models comprises selecting a weight for each of the plurality of computational models to maximize a difference between the plurality of first scores and the plurality of second scores.

6a. The computerized method of any of passages 1a to 5a, wherein generating a biological impact factor comprises determining an inner product between a first vector representative of the first score and a second vector representative of the second score, or wherein generating a biological factor comprises determining a distance between a first surface representative of the first score and a second surface representative of the second score.

7a. The computerized method according to any of passages 1a to 6a, wherein the computational causal network models are selected from two or more of a Cell Proliferation Network, an Inflammatory Process Network, a Cellular Stress Network and a DNA Damage, Autophagy, Cell Death and Senescence Network.

8a. A computer system for determining a biological impact factor, the computer system comprising a processor configured to: receive first data corresponding to a response of a set of biological entities to a first treatment, wherein a biological system comprises a plurality of biological entities including the set of biological entities and wherein each biological entity in the biological system interacts with at least one other of the biological entities in the biological system; receive second data corresponding to a response of the set of biological entities to a second treatment different from the first treatment; provide a plurality of computational causal network models that represent the biological system, each computational model including nodes representing the plurality of biological entities and edges representing relationships between entities in the plurality of biological entities; generate a first score representing the perturbation of the biological system based on the first data and the plurality of computational models, and a second score representing the perturbation of the biological system based on the second data and the plurality of computational models; and generate a biological impact factor based on the first and second scores.

9a. The computer system of passage 8a, wherein each of the first and second scores includes a score vector, and wherein the processor is further configured to: filter the first and second scores to decompose each of the first and second scores into a plurality of projections onto a set of basis vectors; and remove, from at least one of the first and second scores, at least one of the plurality of projections.

10a. The computer system of any of passages 8a or 9a, wherein the set of basis vectors comprise the eigenvectors of a matrix descriptive of at least one of the computational models or wherein generating a biological impact factor comprises determining an inner product between a first vector representative of the first score and a second vector representative of the second score.

11a. The computer system of any of passages 8a to 10a, wherein generating a biological impact factor comprises determining a distance between a first surface representative of the first score and a second surface representative of the second score.

12a. The computerized method according to any of passages 1a to 6a or the computer system according to any of paragraphs 8a to 11a, wherein the biological system includes at least one of a cell proliferation mechanism, a cellular stress mechanism, a cell inflammation mechanism, and a DNA repair mechanism.

13a. The computerized method according to any of passages 1a to 6a or 12a or the computer system according to any of paragraphs 8a to 12a, wherein the first treatment includes at least one of aerosol generated by heating tobacco, exposure to aerosol generated by combusting tobacco, exposure to tobacco smoke, exposure to cigarette smoke, exposure to a heterogeneous substance including a molecule or an entity that is not present in or derived from the biological system, and exposure to at least one of toxins, therapeutic compounds, stimulants, relaxants, natural products, manufactured products, and food substances.

14. A computer program product comprising a program code adapted to perform the method of any of passages 1a to 6a or 12a to 13a.

15. A computer or a computer recordable medium comprising the computer program product according to passage 14a.

While implementations of the present disclosure have been particularly shown and described with reference to specific examples, it should be understood by those skilled in the art that various changes in form and detail may be made therein without departing from the spirit and scope of the present disclosure as defined by the appended claims. The scope of the present disclosure is thus indicated by the appended claims and all changes which come within the meaning and range of equivalency of the claims are therefore intended to be embraced. All publications mentioned in the above specification are herein incorporated by reference.

The invention claimed is:

1. A computerized method for determining an impact of a perturbation on a biological system, the method comprising:
identifying, by a network modeling engine, a plurality of network models that represent the biological system, wherein the biological system comprises a first biological entity and a second biological entity interacting with the first biological entity, wherein the plurality of network models include a first network model and a second network model, wherein each of the first network model and the second network model represents the first biological entity and the second biological entity interacting with the first biological entity such that each of the first network model and the second network includes a first node representing the first biological entity, a second node representing the second biological entity, and a first edge representing a first relationship between the first biological entity and the second biological entity;
updating; by the network modeling engine; the plurality of network models such that either (i) the first node, the second node, or the first edge of the first network model or the second network model is removed, or (ii) a third node representing a third biological entity or a second edge representing a second relationship between the first biological entity and the second biological entity of the first network model or the second network model is added, wherein the second relationship between the first biological entity and the second biological entity is different from the first relationship between the first biological entity and the second biological entity;
generating, from the plurality of network models and a first response of the biological system to a first treatment, by a network scoring engine in communication with the network modeling engine, a first set of scores quantifying the first response of the biological system to the first treatment;
generating, from the plurality of network models and a second response of the biological system to a second treatment, by the network scoring engine, a second set of scores quantifying the second response of the biological system to the second treatment; and
generating, based on a difference between a first multi-dimensional surface defined by the first set of scores and a second multi-dimensional surface defined by the second set of scores, by an aggregation engine in communication with the network scoring engine, a biological impact factor that represents an overall biological impact of the perturbation on the biological system,
wherein at least one of the network modeling engine, the network scoring engine, and the aggregation engine is incorporated on a processor.

2. The method of claim 1, wherein each score in the first set of scores corresponds to a respective network model in the plurality of network models, and generating the first set of scores comprises:
applying a set of weights to a data set corresponding to the first response of the biological system to the first treatment, to obtain a first weighted data set; and
for each respective network model in the plurality of network models,
identifying a portion of the first weighted data set corresponding to the respective network model; and
aggregating the identified portion of the first weighted data set to obtain a respective score in the first set of scores.

3. The method of claim 2, further comprising determining the set of weights based at least in part on a probability that fold change values in the data set corresponding to the first response of the biological system to the first treatment represent a departure from an underlying null hypothesis of a zero fold change.

4. The method of claim 2, further comprising selecting the weights using an optimization technique to obtain a maximal difference between the first set of scores and the second set of scores, wherein the optimization technique includes a constraint on the set of weights.

5. The method of claim 1, wherein the biological impact factor is a scalar value, the method further comprising comparing the biological impact factor with one or more additional biological impact factors that have been obtained in the absence of the perturbation or in the presence of a different perturbation, wherein the generating of the biological impact factor is further based on the comparing.

6. The method of claim 1, wherein the first multi-dimensional surface and second multi-dimensional surface each have a dose dimension and an exposure time dimension.

7. The method of claim 6, further comprising selecting the difference between the first multi-dimensional surface and the second multi-dimensional surface to correspond to a dose and an exposure time at which the first multi-dimensional surface is closest to the second multi-dimensional surface, the first treatment includes exposure to a known toxic substance, and the second treatment includes exposure to an unknown substance.

8. The method of claim 6, further comprising selecting the difference between the first multi-dimensional surface and the second multi-dimensional surface to correspond to a dose and an exposure time at which the first multi-dimensional surface is furthest from the second multi-dimensional surface, the first treatment includes therapy known to be beneficial, and the second treatment includes therapy that is predicted to be beneficial.

9. The method of claim 6, further comprising determining the difference between the first multi-dimensional surface and the second multi-dimensional surface based on closest points on the first multi-dimensional surface and the second multi-dimensional surface, regardless of whether the points correspond to same values in the dose dimension and the exposure time dimension.

10. The method of claim 1, further comprising:
determining a confidence level associated with each one of the first node, the second node, and the first edge of at least one of the first network model or the second network model; and
removing the first node, the second node, or the first edge of the at least one of the first network model or the second network model based on the confidence level associated each of the of the first node, the second node, and the first edge.

11. The method of claim 1, the updating of the plurality of network models further comprising adding the first node, the second node, or the first edge of at least one of the first network model or the second network model based on an unsupervised or supervised learning of the at least one of the first network model or the second network model.

12. A system for determining a biological impact factor, the computer system comprising:
a network modeling engine configured to:
identify, by a network modeling engine, a plurality of network models that represent the biological system, wherein the biological system comprises a first biological entity and a second biological entity interacting with the first biological entity, wherein the plurality of network models include a first network model and a second network model, wherein each of the first network model and the second network model represents the first biological entity and the second biological entity interacting with the first biological entity such that each of the first network model and the second network includes a first node representing the first biological entity, a second node representing the second biological entity, and a first edge representing a first relationship between the first biological entity and the second biological entity; and
update the plurality of network models such that either (i) the first node, the second node, or the first edge of the first network model or the second network model is removed, or (ii) a third node representing a third biological entity or a second edge representing a second relationship between the first biological entity and the second biological entity of the first network model or the second network model is added, wherein the second relationship between the first biological entity and the second biological entity is different from the first relationship between the first biological entity and the second biological entity;
a network scoring engine in communication with the network modeling engine and configured to:
generate, from the plurality of network models and a first response of the biological system to a first treatment, a first set of scores quantifying the first response of the biological system to the first treatment;
generate, from the plurality of network models and a second response of the biological system to a second treatment, a second set of scores quantifying the second response of the biological system to the second treatment; and
an aggregation engine in communication with the network scoring engine and configured to:
generate, based on a difference between a first multi-dimensional surface defined by the first set of scores and a second multi-dimensional surface defined by the second set of scores, a biological impact factor that represents an overall biological impact of a perturbation on the biological system.

13. The system of claim 12, wherein each score in the first set of scores corresponds to a respective network model in the plurality of network models, and for the generating of the first set of scores, the network scoring engine is configured to:
apply a set of weights to a data set corresponding to the first response of the biological system to the first treatment, to obtain a first weighted data set; and
for each respective network model in the plurality of network models,
identify a portion of the first weighted data set corresponding to the respective network model; and
aggregate the identified portion of the first weighted data set to obtain a respective score in the first set of scores.

14. The system of claim 13, the network scoring engine is configured to determine the set of weights based at least in part on a probability that fold change values in the data set corresponding to the first response of the biological system to the first treatment represent a departure from an underlying null hypothesis of a zero fold change.

15. The system of claim 13, wherein the network scoring engine is further configured to select the weights using an optimization technique to obtain a maximal difference between the first set of scores and the second set of scores, wherein the optimization technique includes a constraint on the set of weights.

16. The system of claim 12, wherein the biological impact factor is a scalar value, the network scoring engine is configured to compare the biological impact factor with one or more additional biological impact factors that have been obtained in the absence of the perturbation or in the presence of a different perturbation, wherein the generating of the biological impact factor is further based on the comparing.

17. The system of claim 12, wherein the first multi-dimensional surface and second multi-dimensional surface each have a dose dimension and an exposure time dimension.

18. The system of claim 17, the network scoring engine is configured to select the difference between the first multi-dimensional surface and the second multi-dimensional surface to correspond to a dose and an exposure time at which the first multi-dimensional surface is closest to the second multi-dimensional surface, the first treatment includes exposure to a known toxic substance, and the second treatment includes exposure to an unknown substance.

19. The system of claim 17, the network scoring engine is configured to select the difference between the first multi-dimensional surface and the second multi-dimensional surface to correspond to a dose and an exposure time at which the first multi-dimensional surface is furthest from the second multi-dimensional surface, the first treatment includes therapy known to be beneficial, and the second treatment includes therapy that is predicted to be beneficial.

20. The system of claim 17, the network scoring engine is configured to determine the difference between the first multi-dimensional surface and the second multi-dimensional surface based on closest points on the first multi-dimensional surface and the second multi-dimensional surface, regardless of whether the points correspond to same values in the dose dimension and the exposure time dimension.

* * * * *